US006869694B2

(12) United States Patent
Takiguchi et al.

(10) Patent No.: US 6,869,694 B2
(45) Date of Patent: Mar. 22, 2005

(54) METAL COORDINATION COMPOUND, LUMINESCENCE DEVICE AND DISPLAY APPARATUS

(75) Inventors: Takao Takiguchi, Tokyo (JP); Shinjiro Okada, Isehara (JP); Akira Tsuboyama, Sagamihara (JP); Seishi Miura, Sagamihara (JP); Takashi Moriyama, Kawasaki (JP); Jun Kamatani, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/095,095

(22) Filed: Mar. 12, 2002

(65) Prior Publication Data

US 2003/0085646 A1 May 8, 2003

(30) Foreign Application Priority Data

Mar. 14, 2001 (JP) ........................................ 2001-072665
Feb. 20, 2002 (JP) ........................................ 2002-043536

(51) Int. Cl.$^7$ ........................ H05B 33/14; C09K 11/06; C07D 405/00
(52) U.S. Cl. ........................ 428/690; 428/917; 313/504; 257/88; 546/4; 549/209; 549/212
(58) Field of Search ........................ 428/690, 917; 313/504, 506; 252/301.16; 257/102, 103, 88; 546/4; 549/209, 212

(56) References Cited

U.S. PATENT DOCUMENTS

2001/0019782 A1 * 9/2001 Igarashi et al. ............. 428/690
2002/0125818 A1 * 9/2002 Sato et al. .................. 313/504
2003/0059646 A1 * 3/2003 Kamatani et al. .......... 428/690
2003/0068535 A1 * 4/2003 Takiguchi et al. .......... 428/704

FOREIGN PATENT DOCUMENTS

| EP | 1 191 612 A2 | 3/2002 |
| EP | 1 191 614 A2 | 3/2002 |
| EP | 1 211 257 A2 | 6/2002 |
| EP | 1 238 981 A2 | 9/2002 |
| EP | 1 239 526 A2 | 9/2002 |
| EP | 1 348 711 A1 | 10/2003 |
| EP | 1 349 435 A1 | 10/2003 |
| WO | WO 00/70655 | 11/2000 |
| WO | WO 01/08230 A1 | 2/2001 |

OTHER PUBLICATIONS

D.F. O'Brien, et al., "Improved Energy Transfer in Electro-phosphorescent Devices", Appl. Phys. Lett., vol. 74, No. 3, pp. 422–444 (Jan. 1999).
M.A. Baldo, et al., "Very High–Efficiency Green Organic Light–Emitting Devices Based on Electrophosphores-cence", Appl. Phys. Lett., vol. 75, No. 1, pp. 4–6 (Jul. 1999).
C.H. Chen, et al., "Recent Developments in Molecular Organic Electroluminescent Materials", Macromol. Symp., vol. 125, pp. 1–48 (1997).
P.S. Vincett, et al., "Electrical Conduction and Low Voltage Blue Electroluminescence in Vacuum–Deposited Organic Films", Thin Solid Films, vol. 94, pp. 171–183 (1982).

* cited by examiner

Primary Examiner—Marie Yamnitzky
(74) Attorney, Agent, or Firm—Fitzpatrick, Cella, Harper & Scinto

(57) ABSTRACT

An electroluminescence device having a layer containing a specific metal coordination compound is provided. The metal coordination compound is represented by formula (1) below:

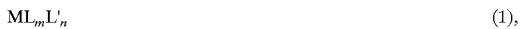

wherein M is a metal atom of Ir, Pt, Rh or Pd; L and L' are mutually different bidentate ligands; m is 1, 2 or 3 and n is 0, 1 or 2 with the proviso that m+n is 2 or 3; a partial structure MLm is represented by formula (2) shown below and a partial structure ML'$_n$ is represented by formula (3) or (4) shown below:

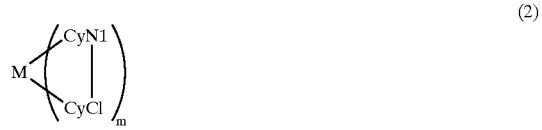

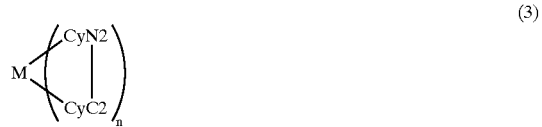

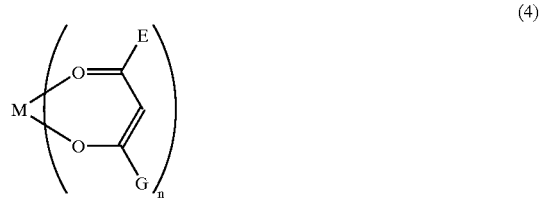

at least one of the optional substituent(s) of the cyclic groups, and the cyclic groups CyC1 and CyC2 includes a benzofuran structure capable of having a substituent represented by the following formula (5):

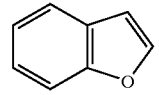

The metal coordination compound having the benzofuran structure is effective in providing high-efficiency lumines-cence and long-term high luminance.

14 Claims, 2 Drawing Sheets

METAL COORDINATION COMPOUND, LUMINESCENCE DEVICE AND DISPLAY APPARATUS

FIELD OF THE INVENTION AND RELATED ART

The present invention relates to an organic luminescence device (also called an organic electroluminescence device or organic EL device) for use in a planar light source, a planar display, etc. Particularly, the present invention relates to a novel metal coordination compound and a luminescence device having a high luminescence efficiency and causing little change with time by using a metal coordination compound represented by formula (1) appearing hereinafter.

An old example of organic luminescence device is, e.g., one using luminescence of a vacuum-deposited anthracene film (Thin Solid Films, 94 (1982) 171). In recent years, however, in view of advantages, such as easiness of providing a large-area device compared with an inorganic luminescence device, and possibility of realizing desired luminescence colors by development of various new materials and drivability at low voltages, an extensive study thereon for device formation as a luminescence device of a high-speed responsiveness and a high efficiency, has been conducted.

As precisely described in Macromol. Symp. 125, 1–48 (1997), for example, an organic EL device generally has an organization comprising a pair of upper and lower electrodes formed on a transparent substrate, and organic material layers including a luminescence layer disposed between the electrodes.

In the luminescence layer, aluminum quinolinol complexes (inclusive of Alq3 shown hereinafter as a representative example) having an electron-transporting characteristic and a luminescence characteristic, are used for example. In a hole-transporting layer, a material having an electron-donative property, such as a triphenyldiamine derivative (inclusive of α-NPD shown hereinafter as a representative example), is used for example.

Such a device shows a current-rectifying characteristic such that when an electric field is applied between the electrodes, holes are injected from the anode and electrons are injected from the cathode.

The injected holes and electrons are recombined in the luminescence layer to form excitons, which emit luminescence when they are transitioned to the ground state.

In this process, the excited states include a singlet state and a triplet state and a transition from the former to the ground state is called fluorescence and a transition from the latter is called phosphorescence. Materials in theses states are called singlet excitons and triplet excitons, respectively.

In most of the organic luminescence devices studied heretofore, fluorescence caused by the transition of a singlet exciton to the ground state, has been utilized. On the other hand, in recent years, devices utilizing phosphorescence via triplet excitons have been studied.

Representative published literature may include:

Article 1: Improved energy transfer in electrophosphorescent device (D. F. O'Brien, et al., Applied Physics Letters, Vol. 74, No. 3, p. 422 (1999)); and Article 2: Very high-efficiency green organic light-emitting devices based on electrophosphorescence (M. A. Baldo, et al., Applied Physics Letters, Vol. 75, No. 1, p. 4 (1999)).

In these articles, a structure including four organic layers sandwiched between the electrodes, and the materials used therein include carrier-transporting materials and phosphorescent materials, of which the names and structures are shown below together with their abbreviations.

Alq3: aluminum quinolinol complex

α-NPD: N4,N4'-di-naphthalene-1-yl-N4,N4'-diphenyl-biphenyl-4,4'-diamine

CBP: 4,4'-N,N'-dicarbazole-biphenyl

BCP: 2,9-dimethyl-4,7-diphenyl-1,10-phenanthroline

PtOEP: platinum-octaethylporphyrin complex

Ir(ppy)$_3$: iridium-phenylpyridine complex

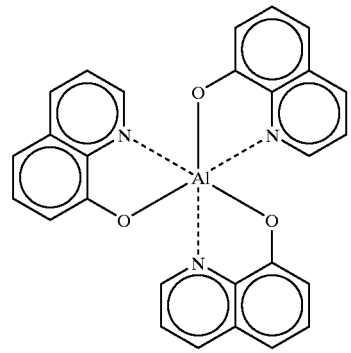

Alq3

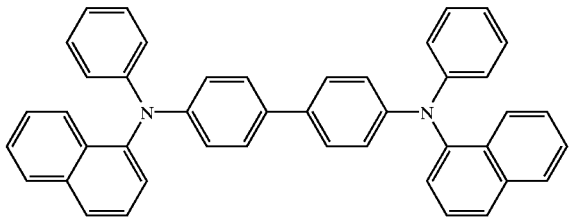

a-NPD

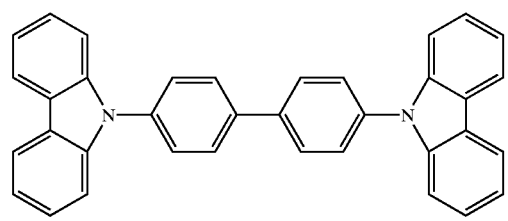

CBP

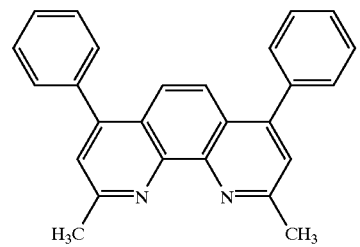

BCP

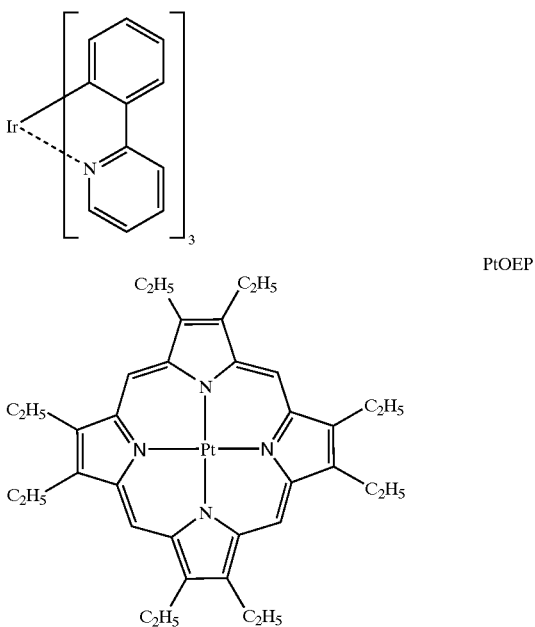

Ir(ppy)₃

PtOEP

The above-mentioned Articles 1 and 2 both have reported structures, as exhibiting a high efficiency, including a hole-transporting layer comprising α-NPD, an electron-transporting layer comprising Alq3, an exciton diffusion-preventing layer comprising BCP, and a luminescence layer comprising CBP as a host and ca. 6% of PtOEP or Ir(ppy)₃ as a phosphorescent material dispersed in mixture therein.

Such a phosphorescent material is particularly noted at present because it is expected to provide a high luminescence efficiency in principle for the following reasons. More specifically, excitons formed by carrier recombination comprise singlet excitons and triplet excitons in a probability ratio of 1:3. Conventional organic EL devices have utilized fluorescence of which the luminescence efficiency is limited to at most 25%. On the other hand, if phosphorescence generated from triplet excitons is utilized, an efficiency of at least three times is expected, and even an efficiency of 100%, i.e., four times, can be expected in principle, if a transition owing to intersystem crossing from a singlet state having a higher energy to a triplet state is taken into account.

However, like a fluorescent-type device, such an organic luminescence device utilizing phosphorescence is generally required to be further improved regarding the deterioration of luminescence efficiency and device stability.

The reason of the deterioration has not been fully clarified, but the present inventors consider as follows based on the mechanism of phosphorescence.

In the case where the luminescence layer comprises a host material having a carrier-transporting function and a phosphorescent guest material, a process of phosphorescence via triplet excitons may include unit processes as follows:

1. transportation of electrons and holes within a luminescence layer,
2. formation of host excitons,
3. excitation energy transfer between host molecules,
4. excitation energy transfer from the host to the guest,
5. formation of guest triplet excitons, and
6. transition of the guest triplet excitons to the ground state and phosphorescence.

Desirable energy transfer in each unit process and luminescence are caused in competition with various energy deactivation processes.

Needless to say, a luminescence efficiency of an organic luminescence device is increased by increasing the luminescence quantum yield of a luminescence center material.

Particularly, in a phosphorescent material, this may be attributable to a life of the triplet excitons which is longer by three or more digits than the life of a singlet exciton. More specifically, because it is held in a high-energy excited state for a longer period, it is liable to react with surrounding materials and cause polymer formation among the excitons, thus incurring a higher probability of deactivation process resulting in a material change or life deterioration.

A luminescence device is desired to exhibit high efficiency luminescence and show a high stability. Particularly, it is strongly desired to provide a luminescence material compound which is less liable to cause energy deactivation in a long life of excited energy state and is also chemically stable, thus providing a longer device life.

SUMMARY OF THE INVENTION

Accordingly, principal objects of the present invention are to provide a luminescence material which exhibits a high luminescence efficiency and retains a high luminance for a long period, and also provide a luminescence device and a display apparatus using the same.

In the present invention, a metal complex is used as a luminescence material, particularly a novel luminescent metal complex compound comprising iridium as a center metal and a benzofuran structure of formula (5) appearing hereinafter as a part of a ligand or as a substituent of a ligand.

More specifically, the present invention provides as a luminescence material a metal coordination compound represented by formula (1) below:

$$ML_mL'_n \qquad (1),$$

wherein M is a metal atom of Ir, Pt, Rh or Pd; L and L' are mutually different bidentate ligands; m is 1, 2 or 3 and n is 0, 1 or 2 with the proviso that m+n is 2 or 3; a partial structure $ML_m$ is represented by formula (2) shown below and a partial structure $ML'_n$ is represented by formula (3) or (4) shown below:

(2)

(3)

(4)

wherein CyN1 and CyN2 are each cyclic group capable of having a substituent, including a nitrogen atom and bonded to the metal atom M via the nitrogen atom; CyC1 and CyC2 are each cyclic group of having a substituent, including a carbon atom and bonded to the metal atom M via the carbon atom with the proviso that the cyclic group CyN1 and the cyclic group CyC1 are bonded to each other via a covalent bond and the cyclic group CyN2 and the cyclic group CyC2 are bonded to each other via a covalent bond;

the optional substituent of the cyclic groups is selected from a halogen atom, cyano group, a nitro group, a trialkylsilyl group of which the alkyl groups are independently a linear or branched alkyl group having 1 to 8 carbon atoms, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom, or an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom);

E and G are independently a linear or branched alkyl group having 1 to 20 carbon atoms of which the alkyl group can include a hydrogen atom that can be optionally replaced with a fluorine atom, or an aromatic group capable of having a substituent (that is a halogen atom, a cyano atom, a nitro atom, a trialkylsilyl group of which the alkyl groups are independently a linear or branched alkyl group having 1–8 carbon atoms, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom; and at least one of the optional substituent(s) of the cyclic groups, and the cyclic groups CyC1 and CyC2 includes a benzofuran structure capable of having a substituent represented by the following formula (5):

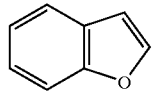

(5)

wherein the benzofuran structure of the formula (5) is bonded to CyN1, CyN2, CyC1 or CyC2 via a single bond at any one of 2- to 7-positions when the benzofuran structure is the optional substituent(s) of the cyclic groups, and the benzofuran structure of the formula (5) is bonded to CyN1 or CyN2 via a single bond at any one of 2- to 7-positions and bonded to the metal atom M via a single bond at any one of 2- to 7-positions when the benzofuran structure is CyC1 or CyC2;

the optional substituent of the benzofuran structure of the formula (5) is selected from a halogen atom, cyano group, a nitro group, a trialkylsilyl group of which the alkyl groups are independently a linear or branched alkyl group having 1 to 8 carbon atoms, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom, or an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom) with the proviso that an adjacent pair of substituents located at 4- to 7-positions of the benzofuran structure of the formula (5) can be bonded to form a cyclic structure.

Preferred embodiments of the metal coordination compound of the formula (1) according to the present invention include the following:

A metal coordination compound, wherein n is 0 in the formula (1).

A metal coordination compound having a partial structure $ML'_n$ represented by the formula (3) in the formula (1).

A metal coordination compound having a partial structure $ML'_n$ represented by the formula (4) in the formula (1).

A metal coordination compound wherein the cyclic groups CyC1 in the formula (1) and CyC2 in the formula (3) are independently selected from phenyl group, thienyl group, thianaphthyl group, naphthyl group, pyrenyl group, 9-fluorenonyl group, fluorenyl group, dibenzofuranyl group, dibenzothienyl group, carbazolyl group, or benzofuranyl group, as an aromatic cyclic group capable of having a substituent with the proviso that the aromatic cyclic group can include one or two CH groups that can be replaced with a nitrogen atom, particularly selected from phenyl group or benzofuranyl group.

A metal coordination compound, wherein the cyclic groups CyN1 in the formula (2) and CyN2 in the formula (3) are independently selected from pyridyl group, pyridazinyl group, and pyrimidinyl group, particularly pyridyl group, as an aromatic cyclic group capable of having a substituent.

A metal coordination compound, wherein the cyclic groups CyN1, CyN2, CyC1 and CyC2 are independently non-substituted, or have a substituent selected from a halogen atom and a linear or branched alkyl group having 1 to 20 carbon atoms {of which the alkyl group can include one or non-neighboring two or more methylene groups that can be replaced with —O—, —S—, —CO—, —CH=CH—, —C≡C—, or a divalent aromatic group capable of having a substituent (that is a halogen atom or a linear or branched alkyl group having 1 to 20 carbon atoms (of which the alkyl group can include one or non-neighboring two or more methylene groups that can be replaced with —O—, and the alkyl group can include a hydrogen atom that can be optionally replaced with a fluorine atom)), and the alkyl group can include a hydrogen atom that can be optionally replaced with a fluorine atom}.

A metal coordination compound, wherein M in the formula (1) is iridium.

A metal coordination compound represented by the following formula (6) or (7), particularly the formula (7):

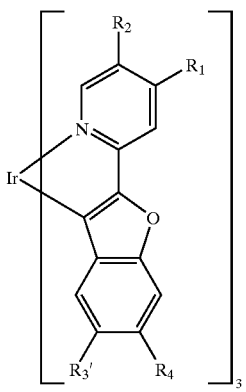

(6)

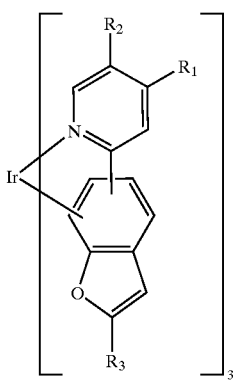

(7)

wherein $R_1$, $R_2$, $R_3$, $R'_3$ and $R_4$ are independently
a hydrogen atom; a fluorine atom; a linear or branched alkyl group of formula: $C_nH_{2n+1}$— in which n is an integer of 1–20, the alkyl group can include one or non-neighboring two or more methylene groups that can be replaced with —O— and also can include a hydrogen atom that can be optionally replaced with a fluorine atom; a phenyl group capable of having a substituent; or a benzofuranyl group capable of having a substituent; the optional substituent of phenyl group and benzofuranyl group is a fluorine atom or a linear or branched alkyl group of formula: $C_nH_{2n+1}$— in which n is an integer of 1–20, the alkyl group can include one or non-neighboring two or more methylene groups that can be replaced with —O— and also can include a hydrogen atom that can be optionally replaced with a fluorine atom.

The present invention also provides an electroluminescence device, comprising: a pair of electrodes disposed on a substrate, and a luminescence unit comprising at least one organic compound disposed between the electrodes, wherein the organic compound comprises a metal coordination compound represented by the formula (1) described above.

In the luminescence device, a voltage is applied between the electrodes to emit phosphorescence.

The present invention further provides a picture display apparatus, comprising an electroluminescence device described above and a means for supplying electric signals to the electroluminescence device.

These and other objects, features and advantages of the present invention will become more apparent upon a consideration of the following description of the preferred embodiments of the present invention taken in conjunction with the accompanying drawings.

DETAILED DESCRIPTION OF THE PREFERRED EMBODIMENTS

Figure 1A:
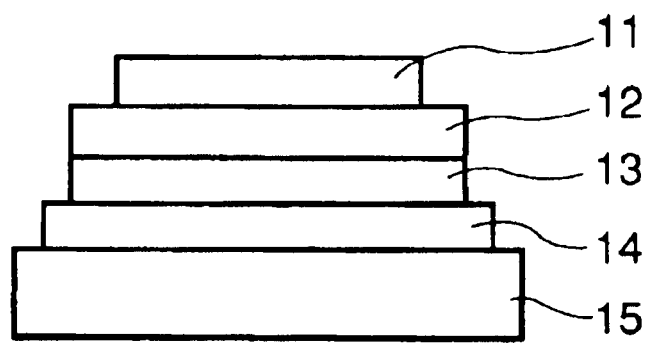
FIGS. 1A, 1B and 1C illustrate embodiments of the luminescence device according to the present invention, respectively.
Figure 1B:
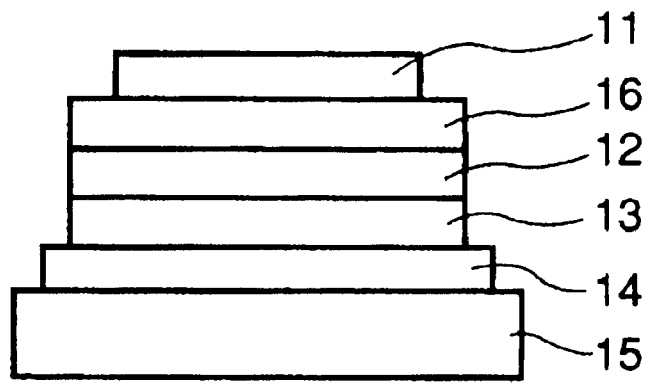
Figure 1C:
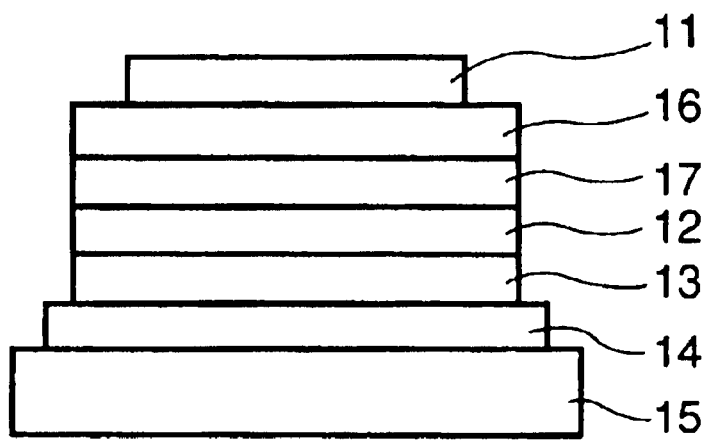

Basic structures of organic luminescence (EL) devices formed according to the present invention are illustrated in FIGS. 1A, 1B and 1C.

As shown in these figures, an organic luminescence device generally comprises, on a transparent substrate 15, a 50 to 200 nm-thick transparent electrode 14, a plurality of organic film layers and a metal electrode 11 formed so as to cover the organic layers.

FIG. 1A shows an embodiment wherein the organic luminescence device comprises a luminescence layer 12 and a hole-transporting layer 13. The transparent electrode 14 may comprise ITO, etc., having a large work function so as to facilitate hole injection from the transparent electrode 14 to the hole-transporting layer 13. The metal electrode 11 comprises a metal material having a small work function, such as aluminum, magnesium or alloys of these elements, so as to facilitate electron injection into the organic luminescence device.

The luminescence layer 12 comprises a compound (metal coordination compound) according to the present invention. The hole-transporting layer 13 may comprise, e.g., a triphenyldiamine derivative, as represented by α-NPD mentioned above, and also a material having an electron-donative property as desired.

A device organized above exhibits a current-rectifying characteristic, and when an electric field is applied between the metal electrode 11 as a cathode and the transparent electrode 14 as an anode, electrons are injected from the metal electrode 11 into the luminescence layer 12, and holes are injected from the transparent electrode 15. The injected holes and electrons are recombined in the luminescence layer 12 to form excitons having high energy potential, which cause luminescence during transition to the ground state. In this instance, the hole-transporting layer 13 functions as an electron-blocking layer to increase the recombination efficiency at the boundary between the luminescence layer layer 12 and the hole-transporting layer 13, thereby providing an enhanced luminescence efficiency.

Further, in the structure of FIG. 1B, an electron-transporting layer 16 is disposed between the metal electrode 11 and the luminescence layer 12 in FIG. 1A. As a result, the luminescence function is separated from the functions of electron transportation and hole transportation to provide a structure exhibiting more effective carrier blocking, thus increasing the luminescence efficiency. The electron-transporting layer 16, may comprise, e.g., an oxadiazole derivative.

FIG. 1C shows another desirable form of a four-layer structure, including a hole-transporting layer 13, a luminescence layer 12, an exciton diffusion prevention layer 17 and an electron-transporting layer 16, successively from the side of the transparent electrode 14 as the anode.

The luminescence materials used in the present invention are most suitably metal coordination compounds represented by the above-mentioned formulae (1) to (5), which are found to cause high-efficiency luminescence, retain high luminance for a long period and show little deterioration by current passage.

The metal coordination compound of the present invention emits phosphorescence, and its lowest excited state is believed to be an MLCT* (metal-to-ligand charge transfer) excited state or π-π* excited state in a triplet state, and phosphorescence is caused at the time of transition from such a state to the ground state.

Hereinbelow, methods for measurement of some properties and physical values described herein for characterizing the luminescence material of the present invention will be described.

(1) Judgment between phosphorescence and fluorescence

The identification of phosphorescence was effected depending on whether deactivation with oxygen was caused or not. A solution of a sample compound in chloroform after aeration with oxygen or with nitrogen is subjected to photoillumination to cause photo-luminescence. The luminescence is judged to be phosphorescence if almost no luminescence attributable to the compound is observed with respect to the solution aerated with oxygen but photo-luminescence is confirmed with respect to the solution aerated with nitrogen. The phosphorescence of all the compounds of the present invention has been confirmed by this method unless otherwise noted specifically.

(2) Phosphorescence yield (a relative quantum yield, i.e., a ratio of an objective sample's quantum yield Φ (sample) to a standard sample's quantum yield Φ (st)) is determined according to the following formula:

$$\Phi(sample)/\Phi(st)=[Sem(sample)/Iabs(sample)]/[Sem(st)/Iabs(st)],$$

wherein Iabs(st) denotes an absorption coefficient at an excitation wavelength of the standard sample; Sem(st), a luminescence spectral areal intensity when excited at the same wavelength; Iabs(sample), an absorption coefficient at an excitation wavelength of an objective compound; and Sem(sample), a luminescence spectral areal intensity when excited at the same wavelength.

Phosphorescence yield values described herein are relative values with respect to a phosphorescence yield Φ=1 of Ir(ppy)$_3$ as a standard sample.

(3) A method of measurement of phosphorescence life is as follows.

A sample compound is dissolved in chloroform and spin-coated onto a quartz substrate in a thickness of ca. 0.1 μm and is exposed to pulsative nitrogen laser light at an excitation wavelength of 337 nm at room temperature by using a luminescence life meter (made by Hamamatsu Photonics K.K.). After completion of the excitation pulses, the decay characteristic of luminescence intensity is measured.

When an initial luminescence intensity is denoted by $I_0$, a luminescence intensity after t(sec) is expressed according to the following formula with reference to a luminescence life τ(sec):

$$I=I_0\cdot\exp(-t/\tau).$$

The luminescence material (metal coordination compound) of the present invention exhibited high phosphorescence quantum yields of 0.11 to 0.9 and short phosphorescence lives of 0.1 to 40 μsec. A short phosphorescence life becomes a condition for causing little energy deactivation and exhibiting an enhanced luminescence efficiency. More specifically if the phosphorescence life is long, the number of triplet state molecules maintained for luminescence is increased, and the deactivation process is liable to occur, thus resulting in a lower luminescence efficiency particularly at the time of a high-current density. The material of the present invention has a relatively short phosphorescence life thus exhibiting a high phosphorescence quantum yield, and is therefore suitable as a luminescence material for an EL device.

As a result of various studies of ours, it has been found that an organic EL device using the metal coordination compound of the formula (1) as a principal luminescence material causes high-efficiency luminescence, retains high luminance for a long period and shows little deterioration by current passage.

In the formula (1) representing the metal coordination compound of the present invention, n may preferably 0 or 1, more preferably 0. Further, the partial structure ML'n may preferably comprise the benzofuran structure represented by the above-mentioned formula (5).

In the present invention, by incorporating the benzofuran structure of the formula (5) into the metal coordination compound of the formula (1), it becomes possible to control an emission wave-length (particularly to provide a long emission wavelength). The presence of the benzofuran structure of the formula (5) is effective in enhancing a solubility of the metal coordination compound of the present invention in an organic solvent, thus facilitating a purification thereof by recrystallization or column chromatography. As a result, the metal coordination compound of the present invention is suitable as a luminescence material for the organic EL device.

Further, as shown in Examples appearing hereinafter, it has been substantiated that the metal coordination compound of the present invention exhibited an excellent stability in a continuous current passage test. This may be attributable to incorporation of the benzofuran structure of the formula (5) into the molecular structure of the metal coordination compound of the formula (1) according to the present invention. More specifically, a change in intermolecular interaction due to the introduction of the benzofuran structure of the formula (5) allows an intermolecular interaction of the metal coordination compound with, e.g., a host material to suppress formation of exciton associates causing thermal deactivation, thus reducing a quenching process thereby to improve phosphorescence yield and device characteristics.

In the case where CyC1 (or CyC2) is benzofuranyl group and CyN1 (or CyN2) is pyridyl or pyrimidinyl group in the metal coordination compound of formula (1) of the present invention, pyridyl or pyrimidinyl group (CyN1 or CyN2) may preferably have a substituent other than methyl group, methoxy group, butyl group and fluorine atom when benzofuran group (CyC1 or CyC2) is not substituted. In another preferred embodiment in the above case, benzofuran group (CyC1 or CyC2) has a substituent, particularly trifluoromethyl group or an aromatic group. In still another preferred embodiment in the above case, the metal coordination compound has a substituent such as trifluoromethyl group, an aromatic group or a cyclized group (e.g., —(CH═CH)$_2$—).

The luminescence device according to the present invention may preferably be an electroluminescence device of the type wherein a layer of the metal coordination compound of the formula (1) is disposed between opposing two electrodes and a voltage is applied between the electrodes to cause luminescence, particularly phosphorescence, as shown in FIGS. 1A, 1B and 1C.

The luminescence device according to the present invention may be applicable to devices required to allow energy saving and high luminance, such as those for display apparatus and illumination apparatus, a light source for printers, and backlight (unit) for a liquid crystal display apparatus.

Specifically, in the case of using the luminescence device of the present invention in the display apparatus, it is possible to provide a flat panel display apparatus capable of exhibiting an excellent energy saving performance, a high visibility and a good lightweight property.

For the application to a display, a drive system using a thin-film transistor (TFT) drive circuit according to an active matrix-scheme may be used. Hereinbelow, an embodiment of using a device of the present invention in combination with an active matrix substrate is briefly described with reference to FIG. 2.

Figure 2:
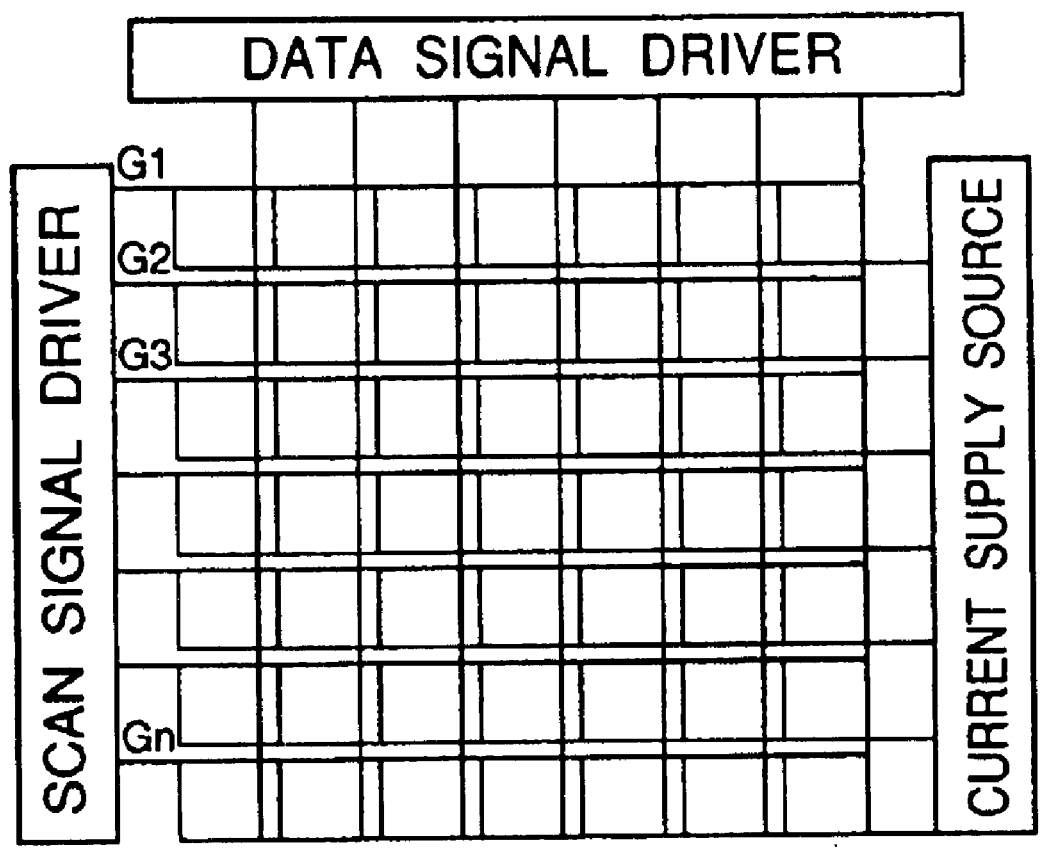
FIG. 2 schematically illustrates a panel structure including an EL device and drive means.

FIG. 2 illustrates an embodiment of panel structure comprising an EL device and drive means. The panel is provided with a scanning signal driver, a data signal driver and a current supply source which are connected to gate selection lines, data signal lines and current supply lines, respectively. At each intersection of the gate selection lines and the data signal lines, a display pixel electrode is disposed. The scanning signal drive sequentially selects the gate selection lines G1, G2, G3 . . . Gn, and in synchronism herewith, picture signals are supplied from the data signal driver to display a picture (image).

By driving a display panel including a luminescence layer comprising a luminescence material of the present invention, it becomes possible to provide a display which exhibits a good picture quality and is stable even for a long period display.

Some synthetic paths for providing a metal coordination compound represented by the above-mentioned formula (1) are illustrated below with reference to an iridium coordination compound (m+n=3) for example:

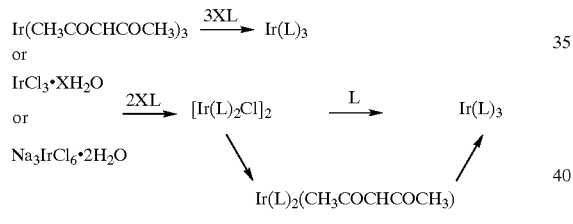

Other metal coordination compound (M=Pt, Rh and Pd) can also be synthesized in a similar manner.

Some specific structural examples of metal coordination compounds used in the present invention are shown in Tables 1 to Tables 17 appearing hereinafter, which are however only representative examples and are not exhaustive. Pi to Bf6 for CyN1, CyN2, CyC1 and CyC2 shown in Tables 1 to 17 represent partial structures shown below.

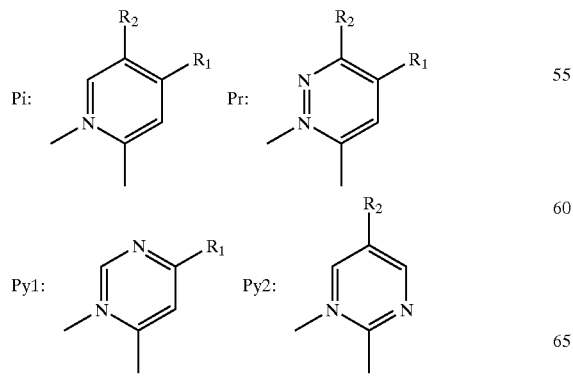

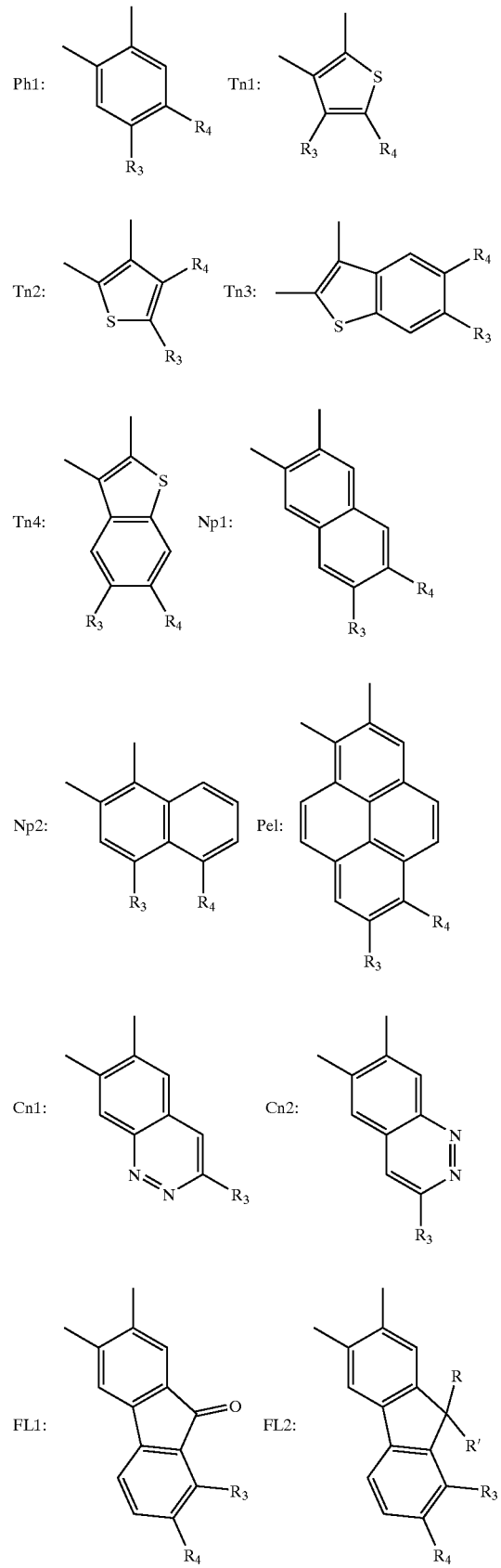

FL3: 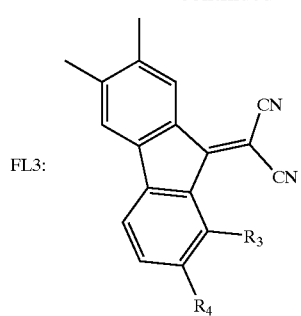
Cz: 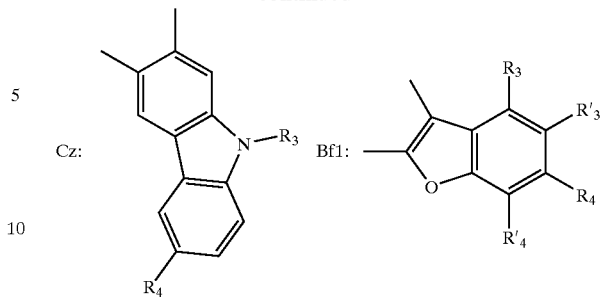
Bf1:
DBF1: 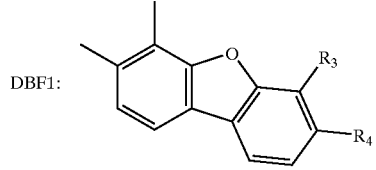
Bf2: 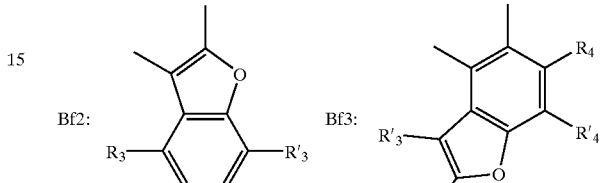 Bf3:
DBT1: 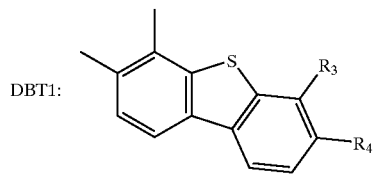
Bf4: 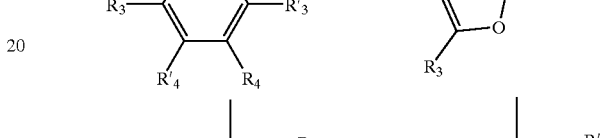 Bf5:
Qn1: 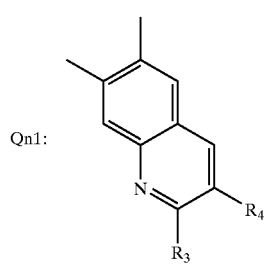  Qn3: 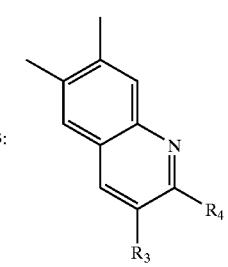
Bf6: 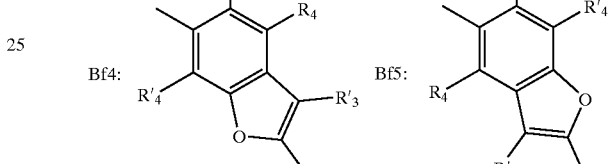
Further, aromatic group Ph2 to Bf8 as substituents for CyN1, CyN2, CyC1 and CyC2 shown in Tables 1 to 17 represent partial structures shown below.
TABLE 1
Ph2: 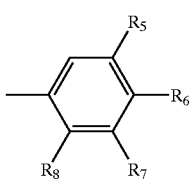  Tn5: 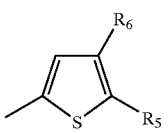  Tn6: 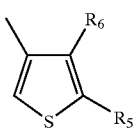
Np3: 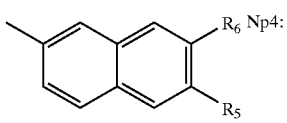  Np4: 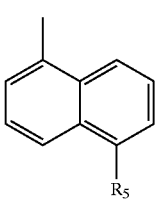  Tn7: 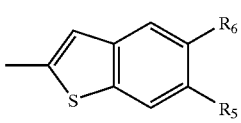

TABLE 1-continued
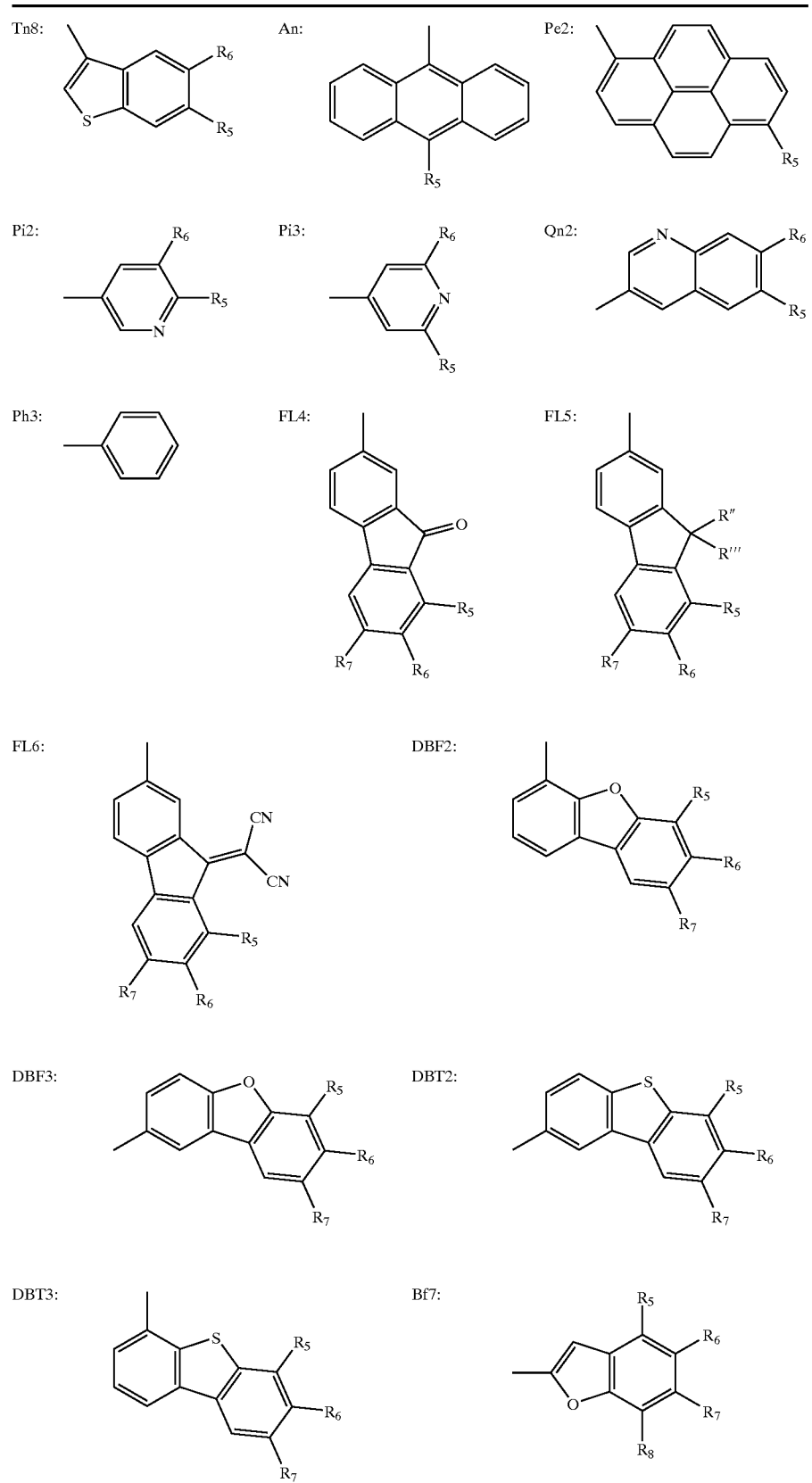

TABLE 1-continued

Bf8: 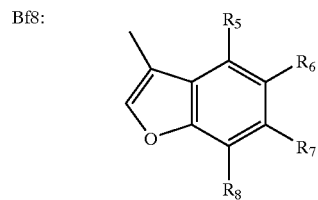

| No | M | m | n | CyN1 | CyC1 | CyN1-R1 CyC1-R3 | CyC1-R4 | CyN1-R2 CyC1-R'3 | CyC1-R'4 | CyN1 R5 CyC1 R5 | R6 R6 | R7 | R8 R7 | R8 |
|---|---|---|---|---|---|---|---|---|---|---|---|---|---|---|
| 1 | Ir | 3 | 0 | Pi | Bf1 | H H | H | H H | H | — | — | — | — | |
| 2 | Ir | 3 | 0 | Pi | Bf1 | CF₃ H | H | H H | H | — | — | — | — | |
| 3 | Ir | 3 | 0 | Pi | Bf1 | CF₃ H | H | CF₃ H | H | — | — | — | — | |
| 4 | Ir | 3 | 0 | Pi | Bf1 | H H | H | CF₃ H | H | — | — | — | — | |
| 5 | Ir | 3 | 0 | Pi | Bf1 | H H | H | NO₂ H | H | — | — | — | — | |
| 6 | Ir | 3 | 0 | Pi | Bf1 | H H | H | Cl H | H | — | — | — | — | |
| 7 | Ir | 3 | 0 | Pi | Bf1 | H H | H | F H | F | — | — | — | — | |
| 8 | Ir | 3 | 0 | Pi | Bf1 | H H | H | CN H | H | — | — | — | — | |
| 9 | Ir | 3 | 0 | Pi | Bf1 | H H | H | OCH₃ H | H | — | — | — | — | |
| 10 | Ir | 3 | 0 | Pi | Bf1 | H H | H | Ph2 H | H | H | H | H | H | |
| 11 | Ir | 3 | 0 | Pi | Bf1 | H H | H | Ph2 H | H | CF₃ | H | H | H | |
| 12 | Ir | 3 | 0 | Pi | Bf1 | H H | H | Ph2 H | H | H | H | F | F | |
| 13 | Ir | 3 | 0 | Pi | Bf1 | Ph2 H | H | H H | H | H | H | H | H | |
| 14 | Ir | 3 | 0 | Pi | Bf1 | H H | H | Np4 H | H | H | — | — | — | |
| 15 | Ir | 3 | 0 | Pi | Bf1 | Tn7 H | H | H H | H | H | H | — | — | |
| 16 | Ir | 3 | 0 | Pi | Bf1 | H H | H | C₄H₉ H | H | — | — | — | — | |
| 17 | Ir | 3 | 0 | Pi | Bf1 | H H | H | H OCH₃ | H | — | — | — | — | |
| 18 | Ir | 3 | 0 | Pi | Bf1 | H H | H | Cl H | H | — | — | — | — | |
| 19 | Ir | 3 | 0 | Pi | Bf1 | H H | H | F H | H | — | — | — | — | |
| 20 | Ir | 3 | 0 | Pi | Bf1 | H H | H | C₈H₁₇ H | H | — | — | — | — | |
| 21 | Ir | 3 | 0 | Pi | Bf1 | H H | H | NO₂ H | H | — | — | — | — | |
| 22 | Ir | 3 | 0 | Pi | Bf1 | H H | H | Ph2 H | H | H | H | H | H | |
| 23 | Ir | 3 | 0 | Pi | Bf1 | H H | H | Ph2 H | H | H | Si(C₃H₇)₃ | H | H | |
| 24 | Ir | 3 | 0 | Pi | Bf1 | Ph2 H | H | Ph2 H | H | H | H | H | H | |
| 25 | Ir | 3 | 0 | Pi | Bf1 | H H | H | Br H | H | — | — | — | — | |
| 26 | Ir | 3 | 0 | Pi | Bf1 | H H | H | Bf7 H | H | H | H | H | H | |
| 27 | Ir | 3 | 0 | Pi | Bf1 | H OC₄H₉ | H | H H | H | — | — | — | — | |
| 28 | Ir | 3 | 0 | Pi | Bf1 | H H | H | Ph2 H | H | H | OCH₂C₅F₁₁ | H | H | |
| 29 | Ir | 3 | 0 | Pi | Bf1 | H H | Br | H H | H | — | — | — | — | |

TABLE 1-continued

| No | M | m | n | CyN1 | CyC1 | R1 / R3 | R4 | R2 / R'3 | R'4 | R5 | R6 | R7 | R8 |
|---|---|---|---|---|---|---|---|---|---|---|---|---|---|
| 30 | Ir | 3 | 0 | Pi | Bf1 | H | | H | | — | — | — | — |
|  |  |  |  |  |  | H | Si(C$_8$H$_{17}$)$_3$ | H | H | — | — | — | — |
| 31 | Ir | 3 | 0 | Pi | Bf2 | H | | H | | — | — | — | — |
|  |  |  |  |  |  | H | H | H | H | — | — | — | — |

TABLE 2

Header structure:
- CyN1-R1 (spans CyC1-R3, CyC1-R4)
- CyN1-R2 (spans CyC1-R'3, CyC1-R'4)
- R5, R6, R7, R8 (upper = CyN1; lower = CyC1)

For each compound, the upper sub-row gives CyN1 substituents (R1, R2, R5, R6, R7, R8) and the lower sub-row gives CyC1 substituents (R3, R4, R'3, R'4, R5, R6, R7, R8).

| No | M | m | n | CyN1 | CyC1 | R1 / R3 | R4 | R2 / R'3 | R'4 | R5 | R6 | R7 | R8 |
|---|---|---|---|---|---|---|---|---|---|---|---|---|---|
| 32 | Ir | 3 | 0 | Pi | Bf2 | CF$_3$ | | H | | — | — | — | — |
|  |  |  |  |  |  | H | H | H | H | — | — | — | — |
| 33 | Ir | 3 | 0 | Pi | Bf2 | CF$_3$ | | CF$_3$ | | — | — | — | — |
|  |  |  |  |  |  | H | H | H | H | — | — | — | — |
| 34 | Ir | 3 | 0 | Pi | Bf2 | H | | CF$_3$ | | — | — | — | — |
|  |  |  |  |  |  | H | H | H | H | — | — | — | — |
| 35 | Ir | 3 | 0 | Pi | Bf2 | Ph2 | | H | | H | H | H | H |
|  |  |  |  |  |  | H | H | H | H | — | — | — | — |
| 36 | Ir | 3 | 0 | Pi | Bf2 | H | | Np4 | | H | — | — | — |
|  |  |  |  |  |  | H | H | H | H | — | — | — | — |
| 37 | Ir | 3 | 0 | Pi | Bf2 | Tn7 | | H | | H | H | — | — |
|  |  |  |  |  |  | H | H | H | H | — | — | — | — |
| 38 | Ir | 3 | 0 | Pi | Bf2 | H | | C$_4$H$_9$ | | — | — | — | — |
|  |  |  |  |  |  | H | H | H | H | — | — | — | — |
| 39 | Ir | 3 | 0 | Pi | Bf2 | H | | H | | — | — | — | — |
|  |  |  |  |  |  | H | H | OCH$_3$ | H | — | — | — | — |
| 40 | Ir | 3 | 0 | Pi | Bf2 | H | | H | | — | Si(C$_3$H$_7$)$_3$ | H | H |
|  |  |  |  |  |  | H | H | Ph2 | H | H | H | H | H |
| 41 | Ir | 3 | 0 | Pi | Bf2 | Ph2 | | H | | H | H | H | H |
|  |  |  |  |  |  | Ph2 | H | H | H | H | H | H | H |
| 42 | Ir | 3 | 0 | Pi | Bf2 | H | | Np3 | | H | H | H | H |
|  |  |  |  |  |  | H | H | H | H | — | — | — | — |
| 43 | Ir | 3 | 0 | Pi | Bf2 | H | | Np4 | | H | — | — | — |
|  |  |  |  |  |  | H | H | H | H | — | — | — | — |
| 44 | Ir | 3 | 0 | Pi | Bf2 | H | | Pe2 | | H | — | — | — |
|  |  |  |  |  |  | H | H | H | H | — | — | — | — |
| 45 | Ir | 3 | 0 | Pi | Bf2 | H | | Qn2 | | H | H | — | — |
|  |  |  |  |  |  | H | H | H | H | — | — | — | — |
| 46 | Ir | 3 | 0 | Pi | Bf2 | H | | An | | H | — | — | — |
|  |  |  |  |  |  | H | H | H | H | — | — | — | — |
| 47 | Ir | 3 | 0 | Pi | Bf2 | H | | Bf7 | | H | H | H | H |
|  |  |  |  |  |  | H | H | H | H | — | — | — | — |
| 48 | Ir | 3 | 0 | Pi | Bf2 | Tn5 | | H | | H | H | — | — |
|  |  |  |  |  |  | H | H | H | H | — | — | — | — |
| 49 | Ir | 3 | 0 | Pi | Bf2 | H | | Bf8 | | H | H | H | H |
|  |  |  |  |  |  | H | H | H | H | — | — | — | — |
| 50 | Ir | 3 | 0 | Pi | Bf2 | H | | Tn6 | | H | H | — | — |
|  |  |  |  |  |  | H | H | H | H | — | — | — | — |
| 51 | Ir | 3 | 0 | Pi | Bf3 | H | | H | | H | OCH$_3$ | H | H |
|  |  |  |  |  |  | Ph2 | H | H | H | H | — | — | — |
| 52 | Ir | 3 | 0 | Pi | Bf3 | H | | CF$_3$ | | — | — | — | — |
|  |  |  |  |  |  | Ph2 | H | H | H | H | OCH$_3$ | H | H |
| 53 | Ir | 3 | 0 | Pi | Bf3 | H | | CF$_3$ | | H | H | — | — |
|  |  |  |  |  |  | Np3 | H | H | H | — | — | — | — |
| 54 | Ir | 3 | 0 | Pi | Bf3 | H | | H | | — | — | — | — |
|  |  |  |  |  |  | H | H | H | H | — | — | — | — |
| 55 | Ir | 3 | 0 | Pi | Bf3 | CF$_3$ | | H | | — | — | — | — |
|  |  |  |  |  |  | C$_2$H$_5$ | H | H | H | — | — | — | — |
| 56 | Ir | 3 | 0 | Pi | Bf3 | CF$_3$ | | CF$_3$ | | — | — | — | — |
|  |  |  |  |  |  | C$_{10}$H$_{21}$ | H | H | H | — | — | — | — |
| 57 | Ir | 3 | 0 | Pi | Bf3 | H | | CF$_3$ | | — | — | — | — |
|  |  |  |  |  |  | H | H | H | H | — | — | — | — |
| 58 | Ir | 3 | 0 | Pi | Bf3 | H | | H | | — | — | — | — |
|  |  |  |  |  |  | Tn5 | H | H | H | H | H | — | — |
| 59 | Ir | 3 | 0 | Pi | Bf3 | H | | H | | — | — | — | — |
|  |  |  |  |  |  | Np3 | H | H | H | H | — | — | — |
| 60 | Ir | 3 | 0 | Pi | Bf3 | H | | H | | — | — | — | — |
|  |  |  |  |  |  | Np4 | H | H | H | H | — | — | — |
| 61 | Ir | 3 | 0 | Pi | Bf4 | H | | CF$_3$ | | — | — | — | — |
|  |  |  |  |  |  | Ph2 | H | H | H | H | C$_6$H$_{13}$ | H | H |

TABLE 3

| No | M | m | n | CyN1 | CyC1 | CyN1-R1 CyC1-R3 | CyN1-R1 CyC1-R4 | CyN1-R2 CyC1-R'3 | CyN1-R2 CyC1-R'4 | CyN1 R5 | CyN1 R6 CyC1 | CyN1 R7 | CyN1 R8 |
|---|---|---|---|---|---|---|---|---|---|---|---|---|---|
| 62 | Ir | 3 | 0 | Pi | Bf4 | H | | H | | — | — | — | — |
| | | | | | | C₈H₁₇ | H | H | H | — | — | — | — |
| 63 | Ir | 3 | 0 | Pi | Bf4 | H | | H | | — | — | — | — |
| | | | | | | Ph2 | H | H | H | H | H | H | H |
| 64 | Ir | 3 | 0 | Pi | Bf4 | Np4 | | H | | H | — | — | — |
| | | | | | | Ph2 | H | H | H | H | H | H | H |
| 65 | Ir | 3 | 0 | Pi | Bf4 | FL4 | | H | | H | H | H | — |
| | | | | | | Ph2 | H | H | H | H | H | H | H |
| 66 | Ir | 3 | 0 | Pi | Bf4 | CF₃ | | CF₃ | | — | — | — | — |
| | | | | | | C₁₅H₃₁ | H | H | H | — | — | — | — |
| 67 | Ir | 3 | 0 | Pi | Bf4 | H | | H | | — | — | — | — |
| | | | | | | DBT2 | H | H | H | H | H | H | — |
| 68 | Ir | 3 | 0 | Pi | Bf4 | H | | Bf7 | | H | H | H | H |
| | | | | | | Ph2 | H | H | H | H | H | H | H |
| 69 | Ir | 3 | 0 | Pi | Bf4 | H | | Bf8 | | H | H | H | H |
| | | | | | | Ph2 | H | H | H | H | H | H | H |
| 70 | Ir | 3 | 0 | Pi | Bf4 | H | | Pi3 | | H | H | H | H |
| | | | | | | Ph2 | H | H | H | H | H | H | H |
| 71 | Ir | 3 | 0 | Pi | Bf5 | H | | CF₃ | | — | — | — | — |
| | | | | | | Ph2 | H | H | H | H | C₆H₁₃ | H | H |
| 72 | Ir | 3 | 0 | Pi | Bf5 | H | | H | | — | — | — | — |
| | | | | | | C₃H₇ | H | H | H | — | — | — | — |
| 73 | Ir | 3 | 0 | Pi | Bf5 | CF₃ | | H | | — | — | — | — |
| | | | | | | C₂₀H₄₁ | H | H | H | — | — | — | — |
| 74 | Ir | 3 | 0 | Pi | Ph1 | H | | Bf7 | | H | H | H | H |
| | | | | | | H | H | — | — | — | — | — | — |
| 75 | Ir | 3 | 0 | Pi | Ph1 | H | | Bf7 | | H | H | H | H |
| | | | | | | H | OCH₃ | — | — | — | — | — | — |
| 76 | Ir | 3 | 0 | Pi | Tn1 | H | | Bf7 | | H | H | H | H |
| | | | | | | H | H | — | — | — | — | — | — |
| 77 | Ir | 3 | 0 | Pi | Np2 | H | | Bf7 | | H | H | H | H |
| | | | | | | H | H | — | — | — | — | — | — |
| 78 | Ir | 3 | 0 | Pi | Cn1 | H | | Bf7 | | H | H | H | H |
| | | | | | | H | H | — | — | — | — | — | — |
| 79 | Ir | 3 | 0 | Pi | DBT1 | H | | Bf7 | | H | H | H | H |
| | | | | | | H | H | — | — | — | — | — | — |
| 80 | Ir | 3 | 0 | Pi | Ph1 | H | | Bf8 | | H | H | H | H |
| | | | | | | H | H | — | — | — | — | — | — |
| 81 | Ir | 3 | 0 | Pi | Ph1 | H | | Bf8 | | H | H | H | H |
| | | | | | | H | H | — | — | — | — | — | — |
| 82 | Ir | 3 | 0 | Pi | Tn2 | H | | Bf8 | | H | H | H | H |
| | | | | | | H | H | — | — | — | — | — | — |
| 83 | Ir | 3 | 0 | Pi | Np2 | H | | Bf8 | | H | H | F | H |
| | | | | | | H | H | — | — | — | — | — | — |
| 84 | Ir | 3 | 0 | Pi | Cn1 | H | | Bf8 | | H | H | H | H |
| | | | | | | H | H | — | — | — | — | — | — |
| 85 | Ir | 3 | 0 | Pi | Cz | H | | Bf8 | | H | H | H | H |
| | | | | | | CH3 | H | — | — | — | — | — | — |
| 86 | Ir | 3 | 0 | Pr | Bf1 | H | | H | | — | — | — | — |
| | | | | | | H | H | H | H | — | — | — | — |
| 87 | Ir | 3 | 0 | Py1 | Bf1 | H | | — | | — | — | — | — |
| | | | | | | H | H | H | H | — | — | — | — |
| 88 | Ir | 3 | 0 | Py2 | Bf1 | — | | H | | — | — | — | — |
| | | | | | | H | H | H | H | — | — | — | — |
| 89 | Ir | 3 | 0 | Pr | Bf2 | H | | H | | — | — | — | — |
| | | | | | | H | H | H | H | — | — | — | — |
| 90 | Ir | 3 | 0 | Py1 | Bf2 | H | | — | | — | — | — | — |
| | | | | | | H | H | H | H | — | — | — | — |
| 91 | Ir | 3 | 0 | Py1 | Bf2 | H | | — | | — | — | — | — |
| | | | | | | —(CH=CH)2- | H | H | H | — | — | — | — |
| 92 | Ir | 3 | 0 | Pi | Bf1 | H | | H | | — | — | — | — |
| | | | | | | H | —(CH=CH)2- | H | H | — | — | — | — |

TABLE 4

| No | M | m | n | CyN1 | CyC1 | CyN1-R1 CyC1-R3 | CyN1-R1 CyC1-R4 | CyN1-R2 CyC1-R'3 | CyN1-R2 CyC1-R'4 | CyN1 R5 | CyN1 R6 CyC1 | R7 | R8 |
|---|---|---|---|---|---|---|---|---|---|---|---|---|---|
| 93 | Ir | 3 | 0 | Pi | Bf1 | H | H | H | —(CH=CH)2— | — | — | — | — |
| 94 | Ir | 3 | 0 | Pi | Bf1 | H —(CH=CH)2— | H H | CF$_3$ H | H H | — | — | — | — |
| 95 | Ir | 3 | 0 | Pi | Bf1 | H H | H —(CH=CH)2— | CF$_3$ H | H H | — | — | — | — |
| 96 | Ir | 3 | 0 | Pi | Bf1 | H H | H H | CF$_3$ —(CH=CH)2— | H H | — | — | — | — |
| 97 | Ir | 3 | 0 | Pi | Bf1 | H —(CH=CH)2— | H H | Np4 H | H H | H — | — | — | — |
| 98 | Ir | 3 | 0 | Pi | Bf1 | H —(CH=CH)2— | H H | Ph2 H | H H | H — | OCH=CHC$_7$H$_{15}$ — | H — | H — |
| 99 | Ir | 3 | 0 | Pi | Bf1 | H H | H —(CH=CH)2— | Ph2 H | H H | H — | OC≡CC$_8$H$_{17}$ — | H — | H — |
| 100 | Ir | 3 | 0 | Pi | Bf1 | Ph2 H | H H | H —(CH=CH)2— | H H | H — | H — | H — | H — |
| 101 | Ir | 3 | 0 | Pi | Bf2 | H H | H —(CH=CH)2— | H H | H H | — | — | — | — |
| 102 | Ir | 3 | 0 | Pi | Bf2 | H H | H H | H —(CH=CH)2— | H H | — | — | — | — |
| 103 | Ir | 3 | 0 | Pi | Bf2 | H H | H —(CH=CH)2— | H H | H H | — | — | — | — |
| 104 | Ir | 3 | 0 | Pi | Bf2 | H H | H H | Np4 —(CH=CH)2— | H H | H — | — | — | — |
| 105 | Ir | 3 | 0 | Pi | Bf2 | H H | H H | Ph2 —(CH=CH)2— | H H | H — | H — | F — | F — |
| 106 | Ir | 3 | 0 | Pi | Bf1 | H —(CH=CH)2— | H H | Np3 H | H H | H — | H — | — | — |
| 107 | Ir | 3 | 0 | Pi | Bf1 | H H | H —(CH=CH)2— | An H | H H | H — | — | — | — |
| 108 | Ir | 3 | 0 | Pi | Bf1 | H H | H H | Pe2 —(CH=)2— | H H | H — | — | — | — |
| 107 | Ir | 3 | 0 | Pi | Bf1 | H H | H —(CH=CH)2— | An H | H H | H — | — | — | — |
| 109 | Ir | 3 | 0 | Pi | Bf1 | H —(CH=CH)2— | H H | Cl H | H H | — | — | — | — |
| 110 | Ir | 3 | 0 | Pi | Bf1 | H H | H —(CH=CH)2— | Tn8 H | H H | H — | H — | — | — |
| 111 | Ir | 3 | 0 | Pi | Bf1 | H H | H H | Pi3 —(CH=CH)2— | H H | H — | H — | — | — |
| 112 | Ir | 3 | 0 | Pi | Bf1 | H —(CH=CH)2— | H H | Qn2 H | H H | H — | H — | — | — |
| 113 | Ir | 3 | 0 | Pi | Bf1 | H —(CH=CH)2— | H H | Ph2 H | H H | H — | OCOC$_7$H$_{15}$ — | H — | H — |
| 114 | Ir | 3 | 0 | Pi | Bf1 | H H | H —(CH=CH)2— | Ph2 H | H H | H — | CN — | H — | H — |
| 115 | Ir | 3 | 0 | Pi | Bf2 | H H | H —(CH=CH)2— | Tn5 H | H H | H — | H — | — | — |
| 116 | Ir | 3 | 0 | Pi | Bf2 | H H | H H | Tn6 —(CH=CH)2— | H H | H — | H — | — | — |
| 117 | Ir | 3 | 0 | Pi | Bf2 | H H | H —(CH=CH)2— | Tn7 H | H H | H — | H — | — | — |
| 118 | Ir | 3 | 0 | Pi | Bf2 | H H | H H | Pi2 —(CH=CH)2— | H H | H — | H — | — | — |
| 119 | Ir | 3 | 0 | Pi | Bf2 | H H | H H | Ph2 —(CH=CH)2— | H H | NO$_2$ — | H — | H — | H — |
| 120 | Ir | 3 | 0 | Pi | Bf2 | H H | H H | DBF3 —(CH=CH)2— | H H | H — | H — | H — | — |
| 121 | Rh | 3 | 0 | Pi | Bf1 | H H | H H | H H | H H | — | — | — | — |
| 122 | Rh | 3 | 0 | Pi | Bf1 | CF$_3$ H | H H | H H | H H | — | — | — | — |

TABLE 5

| | | | | | | CyN1-R1 | | CyN1-R2 | | CyN1 CyC1 | | | |
|---|---|---|---|---|---|---|---|---|---|---|---|---|---|
| No | M | m | n | CyN1 | Cyc1 | CyC1-R3 | CyC1-R4 | CyC1-R'3 | CyC1-R'4 | R5 | R6 | R7 | R8 |
| 123 | Rh | 3 | 0 | Pi | Bf1 | CF₃ | | CF₃ | | — | — | — | — |
| | | | | | | H | H | H | H | | | | |
| 124 | Rh | 3 | 0 | Pi | Bf1 | H | | CF₃ | | — | — | — | — |
| | | | | | | H | H | H | H | | | | |
| 125 | Rh | 3 | 0 | Pi | Bf1 | H | | NO₂ | | — | — | — | — |
| | | | | | | H | H | H | H | | | | |
| 126 | Rh | 3 | 0 | Pi | Bf1 | H | | Cl | | — | — | — | — |
| | | | | | | H | H | H | H | | | | |
| 127 | Rh | 3 | 0 | Pi | Bf1 | H | | F | F | — | — | — | — |
| | | | | | | H | H | H | H | | | | |
| 128 | Rh | 3 | 0 | Pi | Bf1 | H | | CN | | — | — | — | — |
| | | | | | | H | H | H | H | | | | |
| 129 | Rh | 3 | 0 | Pi | Bf1 | H | | OCH₃ | | — | — | — | — |
| | | | | | | H | H | H | H | | | | |
| 130 | Rh | 3 | 0 | Pi | Bf1 | H | | Ph2 | | H | H | H | H |
| | | | | | | H | H | H | H | | | | |
| 131 | Rh | 3 | 0 | Pi | Bf2 | H | | H | | — | — | — | — |
| | | | | | | H | H | H | H | | | | |
| 132 | Rh | 3 | 0 | Pi | Bf2 | CF₃ | | H | | — | — | — | — |
| | | | | | | H | H | H | H | | | | |
| 133 | Rh | 3 | 0 | Pi | Bf2 | CF₃ | | CF₃ | | — | — | — | — |
| | | | | | | H | H | H | H | | | | |
| 134 | Rh | 3 | 0 | Pi | Bf2 | H | | CF₃ | | — | — | — | — |
| | | | | | | H | H | H | H | | | | |
| 135 | Rh | 3 | 0 | Pi | Bf2 | Ph2 | | H | | H | H | H | H |
| | | | | | | H | H | H | H | | | | |
| 136 | Rh | 3 | 0 | Pi | Bf2 | H | | Np4 | | H | — | — | — |
| | | | | | | H | H | H | H | | | | |
| 137 | Rh | 3 | 0 | Pi | Bf2 | Tn7 | | H | | H | H | — | — |
| | | | | | | H | H | H | H | | | | |
| 138 | Rh | 3 | 0 | Pi | Bf2 | H | | C₄H₉ | | — | — | — | — |
| | | | | | | H | H | H | H | | | | |
| 139 | Rh | 3 | 0 | Pi | Bf2 | H | | H | | — | — | — | — |
| | | | | | | H | H | OCH₃ | H | | | | |
| 140 | Rh | 3 | 0 | Pi | Bf2 | H | | H | | — | — | — | — |
| | | | | | | H | H | Ph2 | H | H | Si(C₃H₇)₃ | H | H |
| 141 | Pt | 2 | 0 | Pi | Bf1 | H | | H | | — | — | — | — |
| | | | | | | —(CH=CH)2— | | H | H | | | | |
| 142 | Pt | 2 | 0 | Pi | Bf1 | H | | H | | — | — | — | — |
| | | | | | | H | —(CH=CH)2— | | H | | | | |
| 143 | Pt | 2 | 0 | Pi | Bf1 | H | | H | | — | — | — | — |
| | | | | | | H | H | —(CH=CH)2— | | | | | |
| 144 | Pt | 2 | 0 | Pi | Bf2 | H | | Tn5 | | H | H | — | — |
| | | | | | | H | —(CH=CH)2— | | H | | | | |
| 145 | Pt | 2 | 0 | Pi | Bf2 | H | | Tn6 | | H | H | — | — |
| | | | | | | H | H | —(CH=CH)2— | | | | | |
| 146 | Pt | 2 | 0 | Pi | Bf2 | H | | Tn7 | | H | H | — | — |
| | | | | | | H | —(CH=CH)2— | | H | | | | |
| 147 | Pt | 2 | 0 | Pi | Bf2 | H | | Pi2 | | H | H | — | — |
| | | | | | | H | H | —(CH=)2— | | | | | |
| 148 | Pd | 2 | 0 | Pi | Bf4 | H | | Pi3 | | H | H | — | — |
| | | | | | | Ph2 | H | H | H | H | H | H | H |
| 149 | Pd | 2 | 0 | Pi | Bf5 | H | | CF₃ | | — | — | — | — |
| | | | | | | Ph2 | H | H | H | H | C₆H₁₃ | H | H |
| 150 | Pd | 2 | 0 | Pi | Bf1 | H | | H | | — | — | — | — |
| | | | | | | H | H | Ph2 | H | H | Si(C₃H₇)₃ | H | H |

TABLE 6

| No | M | m | n | CyN1 / CyN2 | CyC1 / CyC2 | CyC1-R3 / CyC2-R3 | CyC1-R4 / CyC2-R4 | CyC1-R'3 / CyC2-R'3 | CyC1-R'4 / CyC2-R'4 | R5 | R6 | R7 | R8 |
|---|---|---|---|---|---|---|---|---|---|---|---|---|---|
| 151 | Ir | 2 | 1 | Pi | Bf1 | H |   | H |   | — | — | — | — |
|  |  |  |  |  |  | H | H | H | H | — | — | — | — |
|  |  |  |  | Pi | Ph'1 | H |   | H |   | — | — | — | — |
|  |  |  |  |  |  | H | H | — | — | — | — | — | — |
| 152 | Ir | 2 | 1 | Pi | Bf1 | $CF_3$ |   | H |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 153 | Ir | 2 | 1 | Pi | Bf1 | $CF_3$ |   | $CF_3$ |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 154 | Ir | 2 | 1 | Pi | Bf1 | H |   | $CF_3$ |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 155 | Ir | 2 | 1 | Pi | Bf1 | H |   | $CF_3$ |   | — | — | — | — |
|  |  |  |  |  |  | H | H | H | H | — | — | — | — |
|  |  |  |  | Pi | Np2 | H |   | H |   | — | — | — | — |
|  |  |  |  |  |  | H | H | — | — | — | — | — | — |
| 156 | Ir | 2 | 1 | Pi | Bf1 | H |   | Ph2 |   | H | H | H | H |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 157 | Ir | 2 | 1 | Pi | Bf2 | H |   | H |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 158 | Ir | 2 | 1 | Pi | Bf2 | $CF_3$ |   | H |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 159 | Ir | 2 | 1 | Pi | Bf2 | $CF_3$ |   | $CF_3$ |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 160 | Ir | 2 | 1 | Pi | Bf2 | H |   | $CF_3$ |   | — | — | — | — |
|  |  |  |  |  |  | H | H | H | H | — | — | — | — |
|  |  |  |  | Pi | Ph1 | H |   | H |   | — | — | — | — |
|  |  |  |  |  |  | H | H | — | — | — | — | — | — |
| 161 | Ir | 2 | 1 | Pi | Bf2 | H |   | $CF_3$ |   | — | — | — | — |
|  |  |  |  |  |  | H | H | H | H | — | — | — | — |
|  |  |  |  | Pi | Ph1 | $CF_3$ |   | H |   | — | — | — | — |
|  |  |  |  |  |  | H | H | — | — | — | — | — | — |

TABLE 7

| No. | M | m | n | CyN1 / CyC1 / CyN2 / CyC2 | | CyN1-R1 / CyC1-R3 / CyN2-R1 / CyC2-R3 | CyN1-R1 / CyC1-R4 / CyN2-R1 / CyC2-R4 | CyN1-R2 / CyC1-R'3 / CyN2-R2 / CyC2-R'3 | CyN1-R2 / CyC1-R'4 / CyN2-R2 / CyC2-R'4 | CyN1/CyC1/CyN2/CyC2 R5 | R6 | R7 | R8 |
|---|---|---|---|---|---|---|---|---|---|---|---|---|---|
| 162 | Ir | 2 | 1 | Pi | Bf2 | H | | Ph2 | H | H | H | H | H |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 163 | Ir | 2 | 1 | Pi | Bf2 | Ph2 | | H | | H | H | H | H |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 164 | Ir | 2 | 1 | Pi | Bf2 | Tn7 | | H | | H | H | — | — |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 165 | Ir | 2 | 1 | Pi | Bf2 | H | | $C_4H_9$ | | — | — | — | — |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 166 | Ir | 2 | 1 | Pi | Bf2 | H | | H | | — | — | — | — |
|  |  |  |  |  |  | H | H | Ph2 | H | H | $Si(C_3H_7)_3$ | H | H |
|  |  |  |  | Pi | Ph1 | H | | H | | — | — | — | — |
|  |  |  |  |  |  | H | H | — | — | — | — | — | — |
| 167 | Ir | 2 | 1 | Pi | Bf2 | Ph2 | | H | | H | H | H | H |
|  |  |  |  |  |  | H | H | Ph2 | H | H | H | H | H |
|  |  |  |  | Pi | Ph1 | H | | H | | — | — | — | — |
|  |  |  |  |  |  | H | H | — | — | — | — | — | — |
| 168 | Ir | 2 | 1 | Pi | Bf2 | H | | Qn2 | | H | H | — | — |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 169 | Ir | 2 | 1 | Pi | Bf2 | H | | Bf7 | | H | H | H | H |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 170 | Ir | 2 | 1 | Pi | Bf2 | H | | Bf8 | | H | H | H | H |
|  |  |  |  |  |  | H | H | H | H | — | — | — | — |
|  |  |  |  | Pi | Ph1 | H | | H | | — | — | — | — |
|  |  |  |  |  |  | H | H | — | — | — | — | — | — |
| 171 | Ir | 2 | 1 | Pi | Bf3 | H | | H | | — | — | — | — |
|  |  |  |  |  |  | Ph2 | H | H | H | H | $OCH_3$ | H | H |
|  |  |  |  | Pi | Ph1 | H | | H | | — | — | — | — |
|  |  |  |  |  |  | H | H | — | — | — | — | — | — |
| 172 | Ir | 2 | 1 | Pi | Bf3 | H | | $CF_3$ | | — | — | — | — |
|  |  |  |  |  |  | Np3 | H | H | H | H | H | — | — |
|  |  |  |  | Pr | Ph1 | H | | H | | — | — | — | — |
|  |  |  |  |  |  | H | H | — | — | — | — | — | — |

TABLE 8

| No | M | m | n | CyN1 / CyC1 / CyN2 / CyC2 | | CyN1-R1 / CyC1-R3 / CyN2-R1 / CyC2-R3 | CyN1-R1 / CyC1-R4 / CyN2-R1 / CyC2-R4 | CyN1-R2 / CyC1-R'3 / CyN2-R2 / CyC2-R'3 | CyN1-R2 / CyC1-R'4 / CyN2-R2 / CyC2-R'4 | CyN1/CyC1/CyN2/CyC2 R5 | R6 | R7 | R8 |
|---|---|---|---|---|---|---|---|---|---|---|---|---|---|
| 173 | Ir | 2 | 1 | Pi | Bf4 | H | | $CF_3$ | | — | — | — | — |
|  |  |  |  |  |  | Ph2 | H | H | H | H | $C_6H_{13}$ | H | H |

TABLE 8-continued

| No | M | m | n | CyN1 CyN2 | CyC1 CyC2 | CyN1-R1 CyC1-R3 CyC2-R3 | CyC1-R4 CyC2-R4 | CyN1-R2 CyC1-R'3 CyC2-R'3 | CyC1-R'4 CyC2-R'4 | CyN1 R5 CyC1 R5 CyC2 R5 | CyN1 R6 CyC1 R6 / CyN2 CyC2 R6 | CyN1 R7 CyC1 R7 CyC2 R7 | CyN1 R8 CyC1 R8 CyC2 R8 |
|---|---|---|---|---|---|---|---|---|---|---|---|---|---|
|  |  |  |  | Py1 |  Ph1 | H | H | — | H | — | — | — | — |
| 174 | Ir | 2 | 1 | Pi | Bf4 | H | H | Bf7 | H | H | H | H | H |
|  |  |  |  | Ph2 |  | H | H | H | H | H | H | H | H |
|  |  |  |  | Py2 | Ph1 | — | H | H | — | — | — | — | — |
| 175 | Ir | 2 | 1 | Pi | Ph1 | H | H | Bf7 | H | H | H | H | H |
|  |  |  |  |  |  | H | OCH₃ | — | — | — | — | — | — |
|  |  |  |  | Pi | Ph1 | H | H | H | — | — | — | — | — |
| 176 | Ir | 2 | 1 | Pi | Np2 | H | H | Bf7 | H | H | H | H | H |
|  |  |  |  |  |  | H | H | — | — | — | — | — | — |
|  |  |  |  | Pi | Ph1 | H | H | H | — | — | — | — | — |
| 177 | Ir | 2 | 1 | Pi | Tn2 | H | H | Bf8 | H | H | H | H | H |
|  |  |  |  |  |  | H | H | — | — | — | — | — | — |
|  |  |  |  | Pi | Ph1 | H | H | H | — | — | — | — | — |
| 178 | Ir | 2 | 1 | Pi | Cn1 | H | H | Bf8 | H | H | H | H | H |
|  |  |  |  |  |  | H | — | — | — | — | — | — | — |
|  |  |  |  | Pi | Ph1 | H | H | Np3 | H | H | H | — | — |
| 179 | Ir | 2 | 1 | Pi | Bf1 | H | H | H | — | — | — | — | — |
|  |  |  |  |  |  | —(CH=CH)2— | H | H | — | — | — | — | — |
|  |  |  |  | Pi | Np2 | H | H | H | — | — | — | — | — |
| 180 | Ir | 2 | 1 | Pi | Bf1 | H | H | H | — | — | — | — | — |
|  |  |  |  |  |  | H | —(CH=CH)2— | H | — | — | — | — | — |
|  |  |  |  | Pi | Ph1 | H | H | CF₃ | — | — | — | — | — |
| 181 | Ir | 2 | 1 | Pi | Bf1 | H | H | H | — | — | — | — | — |
|  |  |  |  |  |  | H | H | —(CH=CH)2— | — | — | — | — | — |
|  |  |  |  | Pi | Bf2 | H | H | CF₃ | — | — | — | — | — |
| 182 | Ir | 2 | 1 | Pi | Bf1 | H | H | CF₃ | — | — | — | — | — |
|  |  |  |  |  |  | —(CH=CH)2— | H | H | — | — | — | — | — |
|  |  |  |  | Pi | Ph1 | H | H | CF₃ | — | — | — | — | — |
| 183 | Ir | 2 | 1 | Pi | Bf1 | H | H | CF₃ | — | — | — | — | — |
|  |  |  |  |  |  | H | —(CH=CH)2— | H | — | — | — | — | — |
|  |  |  |  | Pi | Ph1 | H | H | H | — | — | — | — | — |

TABLE 9

| No | M | m | n | CyN1 CyN2 | CyC1 CyC2 | CyN1-R1 CyC1-R3 CyN2-R1 CyC2-R3 | CyC1-R4 CyC2-R4 | CyN1-R2 CyC1-R'3 CyN2-R2 CyC2-R'3 | CyC1-R'4 CyC2-R'4 | CyN1 R5 CyC1 R5 R5 CyC2 R5 | CyN1 R6 CyC1 R6 R6 CyC2 R6 | R7 R7 R7 | R8 R8 R8 |
|---|---|---|---|---|---|---|---|---|---|---|---|---|---|
| 184 | Ir | 2 | 1 | Pi | Bf1 | H | H | CF₃ | — | — | — | — | — |
|  |  |  |  |  |  | H | H | —(CH=CH)2— | H | — | — | — | — |
|  |  |  |  | Pi | Bf2 | H | H | CF₃ | — | — | — | — | — |
|  |  |  |  |  |  | H | H | H | H | — | — | — | — |
| 185 | Ir | 2 | 1 | Pi | Bf1 | H | H | Np4 | H | H | — | — | — |
|  |  |  |  |  |  | —(CH=CH)2— | H | H | — | — | — | — | — |

TABLE 9-continued

|     |    |   |   |      |      | CyN1-R1 | | CyN1-R2 | | R5 | CyN1 R6 | R7 | R8 |
|-----|----|---|---|------|------|---------|---------|---------|---------|----|----|----|----|
|     |    |   |   |      |      | CyC1- | CyC1- | CyC1- | CyC1- |    | CyC1 | | |
|     |    |   |   | CyN1 | CyC1 | R3 | R4 | R'3 | R'4 | R5 | R6 | R7 | R8 |
|     |    |   |   |      |      | CyN2-R1 | | CyN2-R2 | | R5 | R6 | R7 | R8 |
|     |    |   |   |      |      | CyC2- | CyC2- | CyC2- | CyC2- |    | CyC2 | | |
| No  | M  | m | n | CyN2 | CyC2 | R3 | R4 | R'3 | R'4 | R5 | R6 | R7 | R8 |
|     |    |   |   | Pi | Ph1 | H | H | H | H | — | — | — | — |
|     |    |   |   |    |     | H | H | — | — | — | — | — | — |
| 186 | Ir | 2 | 1 | Pi | Bf1 | H | H | Ph2 | H | H | OCH=CHC$_7$H$_{15}$ | H | H |
|     |    |   |   |    |     | —(CH=CH)2- | | H | H | — | — | — | — |
|     |    |   |   | Pi | Ph1 | H | H | CF$_3$ | — | — | — | — | — |
|     |    |   |   |    |     | H | H | — | — | — | — | — | — |
| 187 | Ir | 2 | 1 | Pi | Bf1 | H | H | Ph2 | H | H | OC≡CC$_8$H$_{17}$ | H | H |
|     |    |   |   |    |     | H | —(CH=CH)2- | H | — | — | — | — | — |
|     |    |   |   | Pi | Np2 | H | H | H | — | — | — | — | — |
|     |    |   |   |    |     | H | H | — | — | — | — | — | — |
| 188 | Ir | 2 | 1 | Pi | Bf1 | Ph2 | H | H | H | H | H | H | H |
|     |    |   |   |    |     | H | H | —(CH=CH)2- | | — | — | — | — |
|     |    |   |   | Pi | Bf2 | H | H | CF$_3$ | H | — | — | — | — |
|     |    |   |   |    |     | H | H | H | H | — | — | — | — |
| 189 | Ir | 2 | 1 | Pi | Bf2 | H | H | H | H | — | — | — | — |
|     |    |   |   |    |     | H | —(CH=CH)2- | H | H | — | — | — | — |
|     |    |   |   | Pi | Ph1 | H | H | H | H | — | — | — | — |
|     |    |   |   |    |     | H | H | — | — | — | — | — | — |
| 190 | Ir | 2 | 1 | Pi | Bf2 | H | H | H | H | — | — | — | — |
|     |    |   |   |    |     | H | H | —(CH=CH)2- | | — | — | — | — |
|     |    |   |   | Pi | Ph1 | H | H | H | H | — | — | — | — |
|     |    |   |   |    |     | H | H | — | — | — | — | — | — |
| 191 | Ir | 2 | 1 | Pi | Bf2 | H | H | H | H | — | — | — | — |
|     |    |   |   |    |     | H | —(CH=CH)2- | H | H | — | — | — | — |
|     |    |   |   | Pi | Ph1 | H | H | H | H | — | — | — | — |
|     |    |   |   |    |     | H | H | — | — | — | — | — | — |
| 192 | Ir | 2 | 1 | Pi | Bf2 | H | H | Np4 | H | H | — | — | — |
|     |    |   |   |    |     | H | H | —(CH=CH)2- | | — | — | — | — |
|     |    |   |   | Pi | Ph1 | H | H | CF$_3$ | H | — | — | — | — |
|     |    |   |   |    |     | H | H | H | H | — | — | — | — |
| 193 | Ir | 2 | 1 | Pi | Bf2 | H | H | Ph2 | H | H | H | F | F |
|     |    |   |   |    |     | H | H | —(CH=CH)2- | | — | — | — | — |
|     |    |   |   | Pi | Bf1 | H | H | H | H | — | — | — | — |
|     |    |   |   |    |     | H | H | — | — | — | — | — | — |
| 194 | Ir | 2 | 1 | Pi | Bf1 | H | H | Np3 | H | H | H | — | — |
|     |    |   |   |    |     | —(CH=CH)2- | | H | H | — | — | — | — |
|     |    |   |   | Pi | Ph1 | H | H | H | H | — | — | — | — |
|     |    |   |   |    |     | H | H | H | H | — | — | — | — |

TABLE 10

|     |    |   |   |      |      | CyN1-R1 | | CyN1-R2 | | R5 | CyN1 R6 | R7 | R8 |
|-----|----|---|---|------|------|---------|---------|---------|---------|----|----|----|----|
|     |    |   |   |      |      | CyC1- | CyC1- | CyC1- | CyC1- |    | CyC1 | | |
|     |    |   |   | CyN1 | CyC1 | R3 | R4 | R'3 | R'4 | R5 | R6 | R7 | R8 |
|     |    |   |   |      |      |    |    |    |    |    | CyN2 | | |
|     |    |   |   |      |      | CyN2-R1 | | CyN2-R2 | | R5 | R6 | R7 | R8 |
|     |    |   |   |      |      | CyC2- | CyC2- | CyC2- | CyC2- |    | CyC2 | | |
| No. | M  | m | n | CyN2 | CyC2 | R3 | R4 | R'3 | R'4 | R5 | R6 | R7 | R8 |
| 195 | Ir | 2 | 1 | Pi | Bf1 | H | H | An | H | H | — | — | — |
|     |    |   |   |    |     | H | —(CH=CH)2- | H | | — | — | — | — |
|     |    |   |   | Pi | Bf2 | H | H | CF$_3$ | H | — | — | — | — |
|     |    |   |   |    |     | H | H | H | H | — | — | — | — |
| 196 | Ir | 2 | 1 | Pi | Bf1 | H | H | Pe2 | H | H | — | — | — |
|     |    |   |   |    |     | H | H | —(CH=CH)2- | | — | — | — | — |
|     |    |   |   | Pi | Ph1 | H | H | CF$_3$ | | — | — | — | — |

TABLE 10-continued

| No. | M | m | n | CyN1 CyC1 CyN2 CyC2 | CyN1-R1 CyC1-R3 | CyN1-R1 CyC1-R4 | CyN1-R2 CyC1-R'3 | CyN1-R2 CyC1-R'4 | R5 CyC1 R5 CyN2 CyC2 R5 | CyN1 R6 CyC1 R6 CyN2 R6 CyC2 | R7 R7 R7 | R8 R8 R8 |
|---|---|---|---|---|---|---|---|---|---|---|---|---|
| 197 | Ir | 2 | 1 | Pi Bf1 | H —(CH=CH)2- | H H | — Cl | — H | — — | — — | — — | — — |
|  |  |  |  | Pi Ph1 | H H | H H | — — | H — | — | — | — | — |
| 198 | Ir | 2 | 1 | Pi Bf1 | H H | H —(CH=CH)2- | — Tn8 | — H | H — | H — | — — | — — |
|  |  |  |  | Pi Ph1 | H H | H H | — — | H — | — | — | — | — |
| 199 | Ir | 2 | 1 | Pi Bf1 | H H | H H | — Pi3 | — —(CH=CH)2- | H — | H — | — — | — — |
|  |  |  |  | Pi DBT-1 | H | H | — | H | — | — | — | — |
| 200 | Ir | 2 | 1 | Pi Bf1 | H —(CH=CH)2- | H H | — Qn2 | — H | H — | H — | — — | — — |
|  |  |  |  | Pi Ph1 | H H | H H | — — | H — | — | — | — | — |
| 201 | Ir | 2 | 1 | Pi Bf1 | H —(CH=CH)2- | H H | — Ph2 H | — H | H — | OCOC$_7$H$_{15}$ — | H — | H — |
|  |  |  |  | Pi Bf2 | H | H | CF$_3$ | H | — | — | — | — |
| 202 | Ir | 2 | 1 | Pi Bf1 | H H | H —(CH=CH)2- | — Ph2 | — H | H — | CN — | H — | H — |
|  |  |  |  | Pi Ph1 | H H | H H | CF$_3$ — | H — | — | — | — | — |
| 203 | Rh | 2 | 1 | Pi Bf2 | H H | H H | — Tn6 —(CH=CH)2- | — H | H — | H — | — — | — — |
|  |  |  |  | Pi Ph1 | H H | H H | — — | H — | — | — | — | — |
| 204 | Rh | 2 | 1 | Pi Bf2 | H H | H H | — Ph2 —(CH=CH)2- | — H | NO$_2$ — | H — | H — | H — |
|  |  |  |  | Pi Ph1 | H H | H H | — — | H — | — | — | — | — |
| 205 | Rh | 2 | 1 | Pi Bf2 | H H | H H | — DBF3 —(CH=CH)2- | — | H — | H — | H — | — — |
|  |  |  |  | Pi Bf2 | H H | H H | CF$_3$ — | H | — | — | — | — |

TABLE 11

| No | M | m | n | CyN1 CyC1 CyN2 CyC2 | CyN1-R1 CyC1-R3 | CyN1-R1 CyC1-R4 | CyN1-R2 CyC1-R'3 | CyN1-R2 CyC1-R'4 | R5 CyC1 R5 CyN2 CyC2 R5 | CyN1 R6 CyC1 R6 CyN2 R6 CyC2 | R7 R7 R7 | R8 R8 R8 |
|---|---|---|---|---|---|---|---|---|---|---|---|---|
| 206 | Rh | 2 | 1 | Pi Bf2 | H H | H H | H Ph2 | H H | — H — | — Si(C$_3$H$_7$)$_3$ — | — H — | — H — |
|  |  |  |  | Pi Ph1 | H | H | — | H | — | — | — | — |
| 207 | Rh | 2 | 1 | Pi Bf2 | Ph2 | H | H | H | H | H | H | H |

TABLE 11-continued

| | | | | | CyN1-R1 | | CyN1-R2 | | CyN1 R5 R6 R7 R8 | | | |
|---|---|---|---|---|---|---|---|---|---|---|---|---|
| | | | | | CyC1-R3 | CyC1-R4 | CyC1-R'3 | CyC1-R'4 | CyC1 R5 R6 R7 R8 | | | |
| | | | CyN1 | CyC1 | | | | | | | | |
| | | | | | CyN2-R1 | | CyN2-R2 | | CyN2 R5 R6 R7 R8 | | | |
| | | | | | CyC2-R3 | CyC2-R4 | CyC2-R'3 | CyC2-R'4 | CyC2 R5 R6 R7 R8 | | | |
| No | M | m | n | CyN2 | CyC2 | R3 | R4 | R'3 | R'4 | R5 | R6 | R7 | R8 |
| | | | | Pi | Ph1 | H | H | Ph2 | H | H | H | H | H |
| | | | | | | H | H | — | — | — | — | — | — |
| 208 | Rh | 2 | 1 | Pi | Bf2 | H | H | Pe2 | H | H | — | — | — |
| | | | | | | H | H | H | H | — | — | — | — |
| | | | | Pi | Ph1 | H | H | CF₃ | H | — | — | — | — |
| | | | | | | H | H | — | — | — | — | — | — |
| 209 | Rh | 2 | 1 | Pi | Bf2 | H | H | An | H | H | — | — | — |
| | | | | | | H | H | H | H | — | — | — | — |
| | | | | Pi | Ph1 | H | H | H | H | — | — | — | — |
| | | | | | | H | H | — | — | — | — | — | — |
| 210 | Rh | 2 | 1 | Pi | Bf2 | H | H | Bf8 | H | H | H | H | H |
| | | | | | | H | H | H | H | — | — | — | — |
| | | | | Pi | Ph1 | H | H | H | H | — | — | — | — |
| | | | | | | H | H | — | — | — | — | — | — |
| 211 | Ir | 1 | 2 | Pi | Bf1 | H | H | H | H | — | — | — | — |
| | | | | | | H | H | H | H | — | — | — | — |
| | | | | Pi | Ph1 | H | H | H | H | — | — | — | — |
| | | | | | | H | H | — | — | — | — | — | — |
| 212 | Ir | 1 | 2 | Pi | Bf1 | CF₃ | H | H | H | — | — | — | — |
| | | | | | | H | H | H | H | — | — | — | — |
| | | | | Pi | Ph1 | H | H | H | H | — | — | — | — |
| | | | | | | H | H | — | — | — | — | — | — |
| 213 | Ir | 1 | 2 | Pi | Bf1 | CF₃ | H | CF₃ | H | — | — | — | — |
| | | | | | | H | H | H | H | — | — | — | — |
| | | | | Pi | Ph1 | H | H | H | H | — | — | — | — |
| | | | | | | H | H | — | — | — | — | — | — |
| 214 | Ir | 1 | 2 | Pi | Bf1 | H | H | CF₃ | H | — | — | — | — |
| | | | | | | H | H | H | H | — | — | — | — |
| | | | | Pi | Ph1 | H | H | H | H | — | — | — | — |
| | | | | | | H | H | — | — | — | — | — | — |
| 215 | Ir | 1 | 2 | Pi | Bf1 | H | H | CF₃ | H | — | — | — | — |
| | | | | | | H | H | H | H | — | — | — | — |
| | | | | Pi | Np2 | H | H | H | H | — | — | — | — |
| | | | | | | H | H | — | — | — | — | — | — |
| 216 | Ir | 1 | 2 | Pi | Bf2 | H | H | H | H | — | — | — | — |
| | | | | | | H | H | H | H | — | — | — | — |
| | | | | Pi | Ph1 | H | H | H | H | — | — | — | — |
| | | | | | | H | H | — | — | — | — | — | — |

TABLE 12

| | | | | | CyN1-R1 | | CyN1-R2 | | R5 | R6 | R7 | R8 |
|---|---|---|---|---|---|---|---|---|---|---|---|---|
| | | | | | CyC1-R3 | CyC1-R4 | CyC1-R'3 | CyC1-R'4 | | CyC1 | | |
| | | | CyN1 | CyC1 | | | | | R5 | R6 | R7 | R8 |
| | | | | | | | | | | CyN2 | | |
| | | | | | CyN2-R1 | | CyN2-R2 | | R5 | R6 | R7 | R8 |
| | | | | | CyC2-R3 | CyC2-R4 | CyC2-R'3 | CyC2-R'4 | | CyC2 | | |
| No | M | m | n | CyN2 | CyC2 | R3 | R4 | R'3 | R'4 | R5 | R6 | R7 | R8 |
| 217 | Ir | 1 | 2 | Pi | Bf2 | CF₃ | H | H | H | — | — | — | — |
| | | | | | | H | H | H | H | — | — | — | — |
| | | | | Pi | Ph1 | H | H | H | H | — | — | — | — |
| | | | | | | H | H | — | — | — | — | — | — |

TABLE 12-continued

| No. | M | m | n | CyN1/CyN2 | CyC1/CyC2 | CyC1-R3/CyC2-R3 | CyC1-R4/CyC2-R4 | CyC1-R'3/CyC2-R'3 | CyC1-R'4/CyC2-R'4 | R5 | R6 | R7 | R8 |
|---|---|---|---|---|---|---|---|---|---|---|---|---|---|
| 218 | Ir | 1 | 2 | Pi | Bf2 | CF$_3$ | H | CF$_3$ | H | — | — | — | — |
|  |  |  |  |  |  | H |  | H |  |  |  |  |  |
|  |  |  |  | Pi | Ph1 | H | H | H | H | — | — | — | — |
|  |  |  |  |  |  | H |  | — |  |  |  |  |  |
| 219 | Ir | 1 | 2 | Pi | Bf2 | H | H | CF$_3$ | H | — | — | — | — |
|  |  |  |  |  |  | H |  | H |  |  |  |  |  |
|  |  |  |  | Pi | Ph1 | H | H | H | H | — | — | — | — |
|  |  |  |  |  |  | H |  | — |  |  |  |  |  |
| 220 | Ir | 1 | 2 | Pi | Bf2 | H | H | CF$_3$ | H | — | — | — | — |
|  |  |  |  |  |  | H |  | H |  |  |  |  |  |
|  |  |  |  | Pi | Ph1 | CF$_3$ | H | H | H | — | — | — | — |
|  |  |  |  |  |  | H |  | H |  |  |  |  |  |
| 221 | Ir | 1 | 2 | Pi | Bf2 | H | H | Ph2 | H | H | H | H | H |
|  |  |  |  |  |  | H |  | H |  |  |  |  |  |
|  |  |  |  | Pi | Ph1 | H | H | H | H | — | — | — | — |
|  |  |  |  |  |  | H |  | — |  |  |  |  |  |
| 222 | Ir | 1 | 2 | Pi | Bf1 | H | —(CH=CH)2— | H | H | — | — | — | — |
|  |  |  |  | Pi | Np2 | H | H | H | H | — | — | — | — |
|  |  |  |  |  |  | H |  | — |  |  |  |  |  |
| 223 | Ir | 1 | 2 | Pi | Bf1 | H | H | H | —(CH=CH)2— | — | — | — | — |
|  |  |  |  | Pi | Ph1 | H | H | CF$_3$ | H | — | — | — | — |
|  |  |  |  |  |  | H |  | H |  |  |  |  |  |
| 224 | Ir | 1 | 2 | Pi | Bf1 | H | H | CF$_3$ | —(CH=CH)2— | — | — | — | — |
|  |  |  |  | Pi | Bf2 | H | H | CF$_3$ | H | — | — | — | — |
|  |  |  |  |  |  | H |  | H |  |  |  |  |  |
| 225 | Ir | 1 | 2 | Pi | Bf1 | H | —(CH=CH)2— | Np4 | H | H | — | — | — |
|  |  |  |  | Pi | Ph1 | H | H | H | H | — | — | — | — |
|  |  |  |  |  |  | H |  | — |  |  |  |  |  |
| 226 | Ir | 1 | 2 | Pi | Bf1 | H | —(CH=CH)2— | Ph2 | H | H | OCH=CHC$_7$H$_{15}$ | H | H |
|  |  |  |  | Pi | Ph1 | H | H | CF$_3$ | H | — | — | — | — |
|  |  |  |  |  |  | H |  | — |  |  |  |  |  |
| 227 | Ir | 1 | 2 | Pi | Bf1 | H | H | Ph2 | H | H | OC≡CC$_8$H$_{17}$ | H | H |
|  |  |  |  |  |  | H | —(CH=CH)2— | H |  |  |  |  |  |
|  |  |  |  | Pi | Np2 | H | H | H | H | — | — | — | — |
|  |  |  |  |  |  | H |  | — |  |  |  |  |  |

TABLE 13

| No. | M | m | n | CyN1/CyN2 | CyC1/CyC2 | CyC1-R3/CyC2-R3 | CyC1-R4/CyC2-R4 | CyC1-R'3/CyC2-R'3 | CyC1-R'4/CyC2-R'4 | R5 | R6 | R7 | R8 |
|---|---|---|---|---|---|---|---|---|---|---|---|---|---|
| 228 | Ir | 1 | 2 | Pi | Bf1 | H | —(CH=CH)2— | Qn2 | H | H | H | — | — |
|  |  |  |  | Pi | Ph1 | H | H | H | H | — | — | — | — |
|  |  |  |  |  |  | H |  | — |  |  |  |  |  |
| 229 | Ir | 1 | 2 | Pi | Bf1 | H | —(CH=CH)2— | Ph2 | H | H | OCOC$_7$H$_{15}$ | H | H |
|  |  |  |  | Pi | Bf2 | H | H | CF$_3$ | H | — | — | — | — |
|  |  |  |  |  |  | H |  | H |  |  |  |  |  |
| 230 | Ir | 1 | 2 | Pi | Bf1 | H | H | Ph2 | H | H | CN | H | H |
|  |  |  |  |  |  | H | —(CH=CH)2— | H |  |  |  |  |  |
|  |  |  |  | Pi | Ph1 | H | H | CF$_3$ | H | — | — | — | — |
|  |  |  |  |  |  | H |  | — |  |  |  |  |  |
| 231 | Ir | 1 | 2 | Pi | Bf2 | H | H | Tn6 | H | H | H | — | — |
|  |  |  |  |  |  | H | H | —(CH=CH)2— |  |  |  |  |  |
|  |  |  |  | Pi | Ph1 | H | H | H | H | — | — | — | — |
|  |  |  |  |  |  | H |  | — |  |  |  |  |  |
| 232 | Ir | 1 | 2 | Pi | Bf2 | H | H | Ph2 | H | NO$_2$ | H | H | H |
|  |  |  |  |  |  | H | H | —(CH=CH)2— |  | — | — | — | — |

TABLE 13-continued

| No | M | m | n | CyN1/CyN2 | CyC1/CyC2 | CyC1-R3/CyC2-R3 | CyC1-R4/CyC2-R4 | CyC1-R'3/CyC2-R'3 | CyC1-R'4/CyC2-R'4 | R5 | R6 | R7 | R8 |
|----|---|---|---|-----------|-----------|-----------------|-----------------|-------------------|-------------------|----|----|----|----|
|    |   |   |   | Pi        | Ph1       | H               |                 | H                 |                   | —  | —  | —  | —  |
|    |   |   |   |           |           | H               | H               | —                 | —                 | —  | —  | —  | —  |
| 233 | Ir | 1 | 2 | Pi        | Bf2       | H               |                 | DBF3              |                   | H  | H  | H  | —  |
|    |   |   |   |           |           | H               | H               | —(CH=CH)2—        |                   | —  | —  | —  | —  |
|    |   |   |   | Pi        | Bf2       | H               |                 | CF₃               |                   | —  | —  | —  | —  |
|    |   |   |   |           |           | H               | H               | H                 | H                 | —  | —  | —  | —  |
| 234 | Ir | 1 | 2 | Pi        | Bf2       | Ph2             |                 | H                 |                   | H  | H  | H  | H  |
|    |   |   |   |           |           | H               | H               | Ph2               | H                 | H  | H  | H  | H  |
|    |   |   |   | Pi        | Ph1       | H               |                 | H                 |                   | —  | —  | —  | —  |
|    |   |   |   |           |           | H               | H               | —                 | —                 | —  | —  | —  | —  |

TABLE 14

| | | | | | | CyN1-R1 | | CyN1-R2 | | R5 | R6 | R7 | R8 |
| | | | | | | CyC1-R3 | CyC1-R4 | CyC1-R'3 | CyC1-R'4 | \multicolumn{4}{c}{CyC1} |
| | | | | CyN1 | CyC1 | | | | | R5 | R6 | R7 | R8 |
| | | | | | | | | | | \multicolumn{4}{c}{CyN2} |
| | | | | | | CyN2-R1 | | CyN2-R2 | | R5 | R6 | R7 | R8 |
| | | | | | | CyC2-R3 | CyC2-R4 | CyC2-R'3 | CyC2-R'4 | \multicolumn{4}{c}{CyC2} |
| No | M | m | n | CyN2 | CyC2 | R3 | R4 | R'3 | R'4 | R5 | R6 | R7 | R8 |
|----|---|---|---|------|------|----|----|-----|-----|----|----|----|----|
| 235 | Rh | 1 | 2 | Pi | Bf2 | H | | Pe2 | | H | — | — | — |
|    |    |   |   |    |     | H | H | H   | H   | — | — | — | — |
|    |    |   |   | Pi | Ph1 | H | | CF₃ | | — | — | — | — |
|    |    |   |   |    |     | H | H | —   | —   | — | — | — | — |
| 236 | Rh | 1 | 2 | Pi | Bf2 | H | | An  | | H | — | — | — |
|    |    |   |   |    |     | H | H | H   | H   | — | — | — | — |
|    |    |   |   | Pi | Ph1 | H | | H   | | — | — | — | — |
|    |    |   |   |    |     | H | H | —   | —   | — | — | — | — |
| 237 | Rh | 1 | 2 | Pi | Bf2 | H | | Bf8 | | H | H | H | H |
|    |    |   |   |    |     | H | H | H   | H   | — | — | — | — |
|    |    |   |   | Pi | Ph1 | H | | H   | | — | — | — | — |
|    |    |   |   |    |     | H | H | —   | —   | — | — | — | — |
| 238 | Rh | 1 | 2 | Pi | Bf1 | Ph2 | | H | | H | H | H | H |
|    |    |   |   |    |     | H | H | —(CH=CH)2— | | — | — | — | — |
|    |    |   |   | Pi | Bf2 | H | | CF₃ | | — | — | — | — |
|    |    |   |   |    |     | H | H | H | H | — | — | — | — |
| 239 | Pt | 1 | 1 | Pi | Bf2 | H | | H | | — | — | — | — |
|    |    |   |   |    |     | H | —(CH=CH)2— | | H | — | — | — | — |
|    |    |   |   | Pi | Ph1 | H | | H | | — | — | — | — |
|    |    |   |   |    |     | H | H | — | — | — | — | — | — |
| 240 | Pd | 1 | 1 | Pi | Bf2 | H | | H | | — | — | — | — |
|    |    |   |   |    |     | H | H | —(CH=CH)2— | | — | — | — | — |
|    |    |   |   | Pi | Ph1 | H | | H | | — | — | — | — |
|    |    |   |   |    |     | H | H | — | — | — | — | — | — |

TABLE 15

| | | | | | | CyN1-R1 | | CyN1-R2 | | R5 | R6 | R7 | R8 |
| | | | | | | CyC1-R3 | CyC1-R4 | CyC1-R'3 | CyC1-R'4 | \multicolumn{4}{c}{CyC1} |
| | | | | CyN1 | CyC1 | R3 | R4 | R'3 | R'4 | R5 | R6 | R7 | R8 |
| | | | | | | | | | | | E | | |
| | | | | E | R" | R''' | | | | R5 | R6 | R7 | R8 |
| | | | | | | | | | | | G | | |
| No | M | m | n | G | R" | R''' | | | | R5 | R6 | R7 | R8 |
|----|---|---|---|---|----|-----|---|---|---|----|----|----|----|
| 241 | Ir | 2 | 1 | Pi | Bf1 | H | | H | | — | — | — | — |
|    |    |   |   |    |     | H | H | H | H | — | — | — | — |
|    |    |   |   | CH₃ |    | — | — | | | — | — | — | — |
|    |    |   |   | CH₃ |    | — | — | | | — | — | — | — |
| 242 | Ir | 2 | 1 | Pi | Bf1 | CF₃ | | H | | — | — | — | — |

TABLE 15-continued

|  |  |  |  |  |  |  | | | | | | | | |
|---|---|---|---|---|---|---|---|---|---|---|---|---|---|---|
|  |  |  |  |  |  | H | H | H | H | — | — | — | — |
|  |  |  |  |  | CF₃ | — | — |  |  | — | — | — | — |
|  |  |  |  |  | CF₃ | — | — |  |  | — | — | — | — |
| 243 | Ir | 2 | 1 | Pi | Bf1 |  | CF₃ |  | CF₃ | — | — | — | — |
|  |  |  |  |  |  | H | H | H | H | — | — | — | — |
|  |  |  |  |  | CH₃ | — | — |  |  | — | — | — | — |
|  |  |  |  |  | CH₃ | — | — |  |  | — | — | — | — |
| 244 | Ir | 2 | 1 | Pi | Bf1 |  | H |  | CF₃ | — | — | — | — |
|  |  |  |  |  |  | H | H | H | H | — | — | — | — |
|  |  |  |  |  | Ph2 | — | — |  |  | H | H | H | H |
|  |  |  |  |  | Ph2 | — | — |  |  | H | H | H | H |
| 245 | Ir | 2 | 1 | Pi | Bf1 |  | H |  | Ph2 | H | H | H | H |
|  |  |  |  |  |  | H | H | H | H | — | — | — | — |
|  |  |  |  |  | Ph2 | — | — |  |  | H | C₃H₇ | H | H |
|  |  |  |  |  | Ph2 | — | — |  |  | H | C₃H₇ | H | H |
| 246 | Ir | 2 | 1 | Pi | Bf2 |  | H |  | H | — | — | — | — |
|  |  |  |  |  |  | H | H | H | H | — | — | — | — |
|  |  |  |  |  | CH₃ | — | — |  |  | — | — | — | — |
|  |  |  |  |  | FL5 | CH₃ | CH₃ |  |  | H | H | H | H |
| 247 | Ir | 2 | 1 | Pi | Bf2 |  | CF₃ |  | H | — | — | — | — |
|  |  |  |  |  |  | H | H | H | H | — | — | — | — |
|  |  |  |  |  | Tn5 | — | — |  |  | H | H | — | — |
|  |  |  |  |  | Tn5 | — | — |  |  | H | H | — | — |
| 248 | Ir | 2 | 1 | Pi | Bf2 |  | CF₃ |  | CF₃ | — | — | — | — |
|  |  |  |  |  |  | H | H | H | H | — | — | — | — |
|  |  |  |  |  | Tn6 | — | — |  |  | H | H | — | — |
|  |  |  |  |  | Tn6 | — | — |  |  | H | H | — | — |
| 249 | Ir | 2 | 1 | Pi | Bf2 |  | H |  | CF₃ | — | — | — | — |
|  |  |  |  |  |  | H | H | H | H | — | — | — | — |
|  |  |  |  |  | CH₃ | — | — |  |  | — | — | — | — |
|  |  |  |  |  | CH₃ | — | — |  |  | — | — | — | — |
| 250 | Ir | 2 | 1 | Pi | Bf2 |  | H |  | Ph2 | H | H | H | H |
|  |  |  |  |  |  | H | H | H | H | — | — | — | — |
|  |  |  |  |  | CF₃ | — | — |  |  | — | — | — | — |
|  |  |  |  |  | CF₃ | — | — |  |  | — | — | — | — |
| 251 | Ir | 2 | 1 | Pi | Bf2 |  | Ph2 |  | H | H | H | H | H |
|  |  |  |  |  |  | H | H | H | H | — | — | — | — |
|  |  |  |  |  | Np3 | — | — |  |  | CH₃O | H | — | — |
|  |  |  |  |  | Np3 | — | — |  |  | CH₃O | H | — | — |

TABLE 16

|  |  |  |  |  |  | CyN1-R1 | | CyN1-R2 | | CyN1 | | | |
|---|---|---|---|---|---|---|---|---|---|---|---|---|---|
|  |  |  |  |  |  | | | | | R5 | R6 | R7 | R8 |
|  |  |  |  |  |  | CyC1- | CyC1- | CyC1- | CyC1- | CyC1 | | | |
|  |  |  |  | CyN1 | CyC1 | R3 | R4 | R'3 | R'4 | R5 | R6 | R7 | R8 |
|  |  |  |  |  |  |  |  |  |  | E | | | |
|  |  |  |  |  | E | R" | R''' |  |  | R5 | R6 | R7 | R8 |
|  |  |  |  |  |  |  |  |  |  | G | | | |
| No | M | m | n | G |  | R" | R''' |  |  | R5 | R6 | R7 | R8 |
| 252 | Ir | 2 | 1 | Pi | Bf2 | Tn7 |  | H |  | H | H | — | — |
|  |  |  |  |  |  | H | H | H | H | — | — | — | — |
|  |  |  |  |  | Np4 | — | — |  |  | F | — | — | — |
|  |  |  |  |  | Np4 | — | — |  |  | F | — | — | — |
| 253 | Ir | 2 | 1 | Pi | Bf2 |  | H |  | C₄H₉ | — | — | — | — |
|  |  |  |  |  |  | H | H | H | H | — | — | — | — |
|  |  |  |  |  | Tn7 | — | — |  |  | CH₃ | H | — | — |
|  |  |  |  |  | Tn7 | — | — |  |  | CH₃ | H | — | — |
| 254 | Ir | 2 | 1 | Pi | Bf2 |  | H |  | H | — | — | — | — |
|  |  |  |  |  |  | H | H | Ph2 | H | H | Si(C₃H₇)₃ | H | H |
|  |  |  |  |  | Tn8 | — | — |  |  | H | H | — | — |
|  |  |  |  |  | Tn8 | — | — |  |  | H | H | — | — |
| 255 | Ir | 2 | 1 | Pi | Bf2 |  | Ph2 |  | H | H | H | H | H |
|  |  |  |  |  |  | H | H | Ph2 | H | H | H | H | H |
|  |  |  |  |  | Pe2 | — | — |  |  | H | — | — | — |
|  |  |  |  |  | Pe2 | — | — |  |  | H | — | — | — |
| 256 | Ir | 2 | 1 | Pi | Bf2 |  | H |  | Qn2 | H | H | — | — |
|  |  |  |  |  |  | H | H | H | H | — | — | — | — |
|  |  |  |  |  | Pi2 | — | — |  |  | — | — | H | H |
|  |  |  |  |  | Pi2 | — | — |  |  | — | — | H | — |

TABLE 16-continued

| No | M | m | n | CyN1 | CyC1 | CyN1-R1 CyC1-R3 | CyN1-R2 CyC1-R4 | R5 | R6 | R7 | R8 |
|---|---|---|---|---|---|---|---|---|---|---|---|
|   |   |   |   |   | E | R" | R'" | R5 | R6 | R7 | R8 |
|   |   |   |   |   | G | R" | R'" | R5 | R6 | R7 | R8 |
| 257 | Ir | 2 | 1 | Pi | Bf2 | H | Bf7 | H | H | H | H |
|   |   |   |   |   |   | H H | H H | — | — | — | — |
|   |   |   |   |   | Pi3 | — | — | CH₃ | CH₃ | H | H |
|   |   |   |   |   | Pi3 | — | — | CH₃ | CH₃ | H | H |
| 258 | Ir | 2 | 1 | Pi | Bf2 | H | Bf8 | H | H | H | H |
|   |   |   |   |   |   | H H | H H | — | — | — | — |
|   |   |   |   |   | FL4 | — | — | H | H | H | — |
|   |   |   |   |   | FL4 | — | — | H | H | H | — |
| 259 | Ir | 2 | 1 | Pi | Bf3 | H | H | — | — | — | — |
|   |   |   |   |   |   | Ph2 H | H H | H | OCH₃ | H | H |
|   |   |   |   |   | FL5 | C2H5 | C2H5 | H | H | H | — |
|   |   |   |   |   | FL5 | (CH2)5Ph3 | (CH2)5Ph3 | H | H | H | — |
| 260 | Ir | 2 | 1 | Pi | Bf4 | H | CF₃ | — | — | — | — |
|   |   |   |   |   |   | Ph2 H | H H | H | C₆H₁₃ | H | H |
|   |   |   |   |   | DBF2 | — | — | H | H | H | — |
|   |   |   |   |   | DBF2 | — | — | H | H | H | — |
| 261 | Ir | 2 | 1 | Pi | Ph1 | H | Bf7 | H | H | H | H |
|   |   |   |   |   |   | H OCH₃ | — — | — | — | — | — |
|   |   |   |   |   | DBT3 | — | — | H | H | H | H |
|   |   |   |   |   | DBT3 | — | — | H | H | H | H |
| 262 | Rh | 2 | 1 | Pi | Bf1 | H | H | — | — | — | — |
|   |   |   |   |   |   | —(CH=CH)2— | H H | — | — | — | — |
|   |   |   |   |   | CH₃ | — | — | — | — | — | — |
|   |   |   |   |   | CH₃ | — | — | — | — | — | — |

TABLE 17

| | | | | | | CyN1-R1 | CyN1-R2 | R5 | CyN1 R6 | R7 | R8 |
|---|---|---|---|---|---|---|---|---|---|---|---|
| | | | | | | CyC1-R3 | CyC1-R4 | R5 | CyC1 R6 | R7 | R8 |
| | | | | CyN1 | CyC1 | | | | E | | |
| | | | | | E | R" | R'" | R5 | R6 | R7 | R8 |
| No | M | m | n | | G | R" | R'" | R5 | G R6 | R7 | R8 |
| 263 | Rh | 2 | 1 | Pi | Bf1 | H | H | — | — | — | — |
|   |   |   |   |   |   | H —(CH=CH)2— | H | — | — | — | — |
|   |   |   |   |   | CF₃ | — | — | — | — | — | — |
|   |   |   |   |   | CF₃ | — | — | — | — | — | — |
| 264 | Rh | 2 | 1 | Pi | Bf1 | H | H | — | — | — | — |
|   |   |   |   |   |   | H H | —(CH=CH)2— | — | — | — | — |
|   |   |   |   |   | Qn2 | — | — | H | H | — | — |
|   |   |   |   |   | Qn2 | — | — | H | H | — | — |
| 265 | Rh | 2 | 1 | Pi | Bf2 | H | CF₃ | — | — | — | — |
|   |   |   |   |   |   | H H | H H | — | — | — | — |
|   |   |   |   |   | Np3 | — | — | H | H | — | — |
|   |   |   |   |   | Np3 | — | — | H | H | — | — |
| 266 | Pt | 1 | 1 | Pi | Bf1 | H | CF₃ | — | — | — | — |
|   |   |   |   |   |   | H H | —(CH=CH)2— | — | — | — | — |
|   |   |   |   |   | CH₃ | — | — | — | — | — | — |
|   |   |   |   |   | CH₃ | — | — | — | — | — | — |
| 267 | Pt | 1 | 1 | Pi | Bf1 | H | Np4 | H | — | — | — |
|   |   |   |   |   |   | —(CH=CH)2— | H H | — | — | — | — |
|   |   |   |   |   | CF₃ | — | — | — | — | — | — |
|   |   |   |   |   | CF₃ | — | — | — | — | — | — |
| 268 | Pd | 1 | 1 | Pi | Bf1 | H | Ph2 | H | OCH=CHC₇H₁₅ | H | H |
|   |   |   |   |   |   | —(CH=CH)2— | H H | — | — | — | — |
|   |   |   |   |   | CH₃ | — | — | — | — | — | — |
|   |   |   |   |   | CH₃ | — | — | — | — | — | — |
| 269 | Pd | 1 | 1 | Pi | Bf2 | H | CF₃ | — | — | — | — |
|   |   |   |   |   |   | H H | H H | — | — | — | — |
|   |   |   |   |   | CF₃ | — | — | — | — | — | — |
|   |   |   |   |   | CF₃ | — | — | — | — | — | — |
| 270 | Ir | 1 | 2 | Pi | Bf1 | H | Ph2 | H | OC≡CC₈H₁₇ | H | H |
|   |   |   |   |   |   | H —(CH=CH)2— | H | — | — | — | — |
|   |   |   |   |   | CH₃ | — | — | — | — | — | — |
|   |   |   |   |   | CH₃ | — | — | — | — | — | — |

In the case where the metal coordination compound of the formula (1) is used as a luminescent material, the metal coordination compound used singly (as a single luminescent material) or in combination with another luminescent material (host compound).

In the latter case, the resultant luminescence material (composition or mixture) may preferably contain the metal coordination compound of the formula (1) in an amount of at most 50 wt. %, more preferably 0.1–20 wt. %. Above 50 wt. %, a resultant luminescence strength is undesirably be lowered due to quenching with an increasing concentration in some cases.

Hereinbelow, the present invention will be described more specifically based on Examples.

EXAMPLE 1

Synthesis of Example Compound No. 34

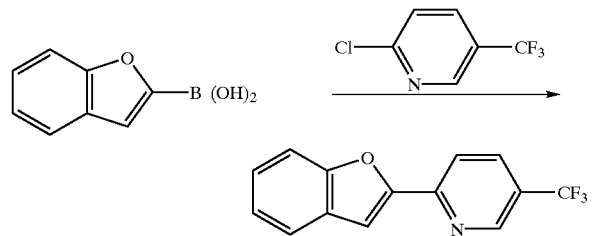

In a 100 ml-three-necked flask, 2.80 g (15.4 mM) of 2-chloro-5-trifluoromethylpyridine, 2.50 g (15.4 mM) of 2-benzofuranylboronic acid, 14 ml of toluene, 7 ml of ethanol and 14 ml of 2M-sodium carbonate aqueous solution were placed and stirred at room temperature under nitrogen stream, and 0.55 g (0.48 mM) of tetrakis (triphenylphosphine)palladium (0) was added thereto. Thereafter, reflux under stirring for 4 hours was performed under nitrogen stream. After the reaction, the reaction mixture was cooled on an ice bath and stirred at room temperature after addition of ethyl acetate and saturated saline water. The organic layer was washed with water and dried with anhydrous magnesium sulfate, and the solvent was removed under reduced pressure to obtain a residue. The residue was purified by alumina column chromatography (eluent: toluene) and recrystallized from methanol to obtain 0.72 g of 2-(5-trifluoromethylpyridine-2-yl)benzofuran (Yield: 17.7%).

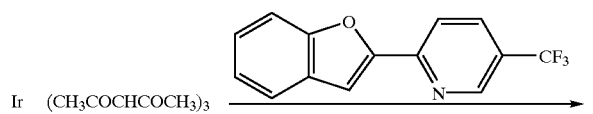

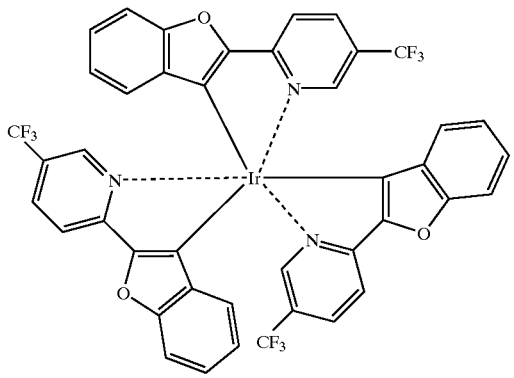

In a 100 ml-four-necked flask, 25 ml of glycerol was placed and heated at 130–140° C. under stirring and bubbling with nitrogen for 2 hours. Then, the glycerol was cooled by standing down to 100° C., and 0.70 g (2.66 mM) of 2-(5-trifluoromethylpyridine-2-yl)benzofuran and 0.23 g (0.47 mM) of iridium (III) acetylacetonate were added, followed by 7 hours and 10 minutes of heating at 192–230° C. under stirring and nitrogen stream. The reaction product was cooled to room temperature and injected into 150 ml of 1N-hydrochloric acid to form a precipitate, which was filtered out, washed with water, and dissolved in acetone to remove the insoluble content. The acetone was distilled off under reduced pressure to obtain a residue. The residue was washed with methanol and purified by silica gel column chromatography with toluene as the eluent to obtain 0.11 g (yield=23.4%) of red powdery tris[2-(benzofuran-2-yl)-5-trifluoromethyl-pyridine-$C^3$,N]iridium (III).

A toluene solution of the compound exhibited a photoluminescence spectrum showing $\lambda$max (maximum emission wavelength)=622 nm and a quantum yield of 0.12.

EXAMPLES 2–10

Each of luminescence devices having a layer structure shown in FIG. 1B were prepared in the following manner.

On a 1.1 mm-thick glass substrate (transparent substrate 15), a 100 nm-thick film (transparent electrode 14) of ITO (indium tin oxide) was formed by sputtering, followed by patterning to form a stripe electrode including 100 lines each having a width of 100 nm and a spacing with an adjacent line of 10 nm (i.e., electrode pitch of 110 nm).

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (30 nm): co-deposited film of CBP:metal complex (metal coordination compound shown in Table 18) (95:5 by weight)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

The above-deposited metal electrode layers 1 and 2 (Al—Li layer and Al layer) had a stripe electrode pattern including 100 lines each having a width of 100 nm and a spacing of 10 nm (electrode pitch=110 nm) and arranged so that the stripe electrode pattern intersected with that of the ITO electrode at right angles to form a matrix of pixels each having an effective electrode area of 3 mm² comprising 20 ITO lines bundled together at a lead-out portion and 15 Al (Al—Li) lines bundled together at a lead-out portion.

Each of the thus-prepared luminescence devices was taken out of the vacuum chamber and was subjected to a continuous energization (current passage) test in an atmosphere of dry nitrogen gas stream so as to remove device deterioration factors, such as oxygen and moisture (water content).

The continuous energization test was performed by continuously applying a voltage at a constant current density of 70 mA/cm² to the luminescence device having the ITO (transparent) electrode (as an anode) and the Al (metal) electrode (as a cathode), followed by measurement of emission luminance (brightness) with time so as to determine a time (luminance half-life) required for decreasing an initial luminance (80–250 cd/m²) to ½ thereof.

The results are shown in Table 18 appearing hereinafter.

COMPARATIVE EXAMPLE 1

A comparative luminescence device was prepared and evaluated in the same manner as in Examples 2–10 except that the Ir complexes (metal coordination compounds shown in Table 185) was changed to Ir-phenylpyridine complex (Ir(ppy)₃) shown below.

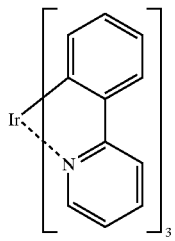

The results are also also shown in Table 18 below.

TABLE 18

| Ex. No. | Compound No. | Luminance half-life (Hr) |
|---|---|---|
| Ex. 2 | 4 | 800 |
| Ex. 3 | 10 | 900 |
| Ex. 4 | 31 | 750 |
| Ex. 5 | 34 | 900 |
| Ex. 6 | 92 | 800 |
| Ex. 7 | 115 | 650 |
| Ex. 8 | 135 | 750 |
| Ex. 9 | 156 | 850 |
| Ex. 10 | 238 | 600 |
| Comp. Ex. 1 | Ir (ppy)₃ | 350 |

As is apparent from Table 18, compared with the conventional luminescence device using Ir(ppy)₃, the luminescence devices using the metal coordination compounds of formula (1) according to the present invention provide longer luminance half-lives, thus resulting in an EL device having a high durability (luminance stability) based on a good stability of the metal coordination compound of formula (1) of the present invention.

EXAMPLE 11

A color organic EL display apparatus shown in FIG. 2 was prepared in the following manner.

An active matrix substrate had a planar structure basically similar to a structure described in U.S. Pat. No. 6,114,715.

Specifically, on a 1.1 mm-thick glass substrate, top gate-type TFTs of polycrystalline silicon were formed in an ordinary manner and thereon, a flattening film was formed with contact holes for electrical connection with a pixel electrode (anode) at respective source regions, thus preparing an active matrix substrate with a TFT circuit.

On the active matrix substrate, a 700 nm-thick pixel electrode (anode) of ITO having a large work function was formed in a prescribed pattern. On the ITO electrode, prescribed organic layers and a 100 nm-thick Al electrode (cathode) were successively formed by vacuum deposition with a hard mask, followed by patterning to form a matrix of color pixels (128×128 pixels).

The respective organic layers corresponding to three color pixels (red (R) green (G) and blue (B)) were consisting of the following layers.

<R Pixel Region>
α-NPD (40 nm)/CBP: Ex. Comp. No. 34 (93:7 by weight) (30 nm)/BCP (20 nm)/Alq 3 (40 nm)

<G Pixel Region>
α-NPD (50 nm)/Alq 3 (50 nm)

<B Pixel Region>
α-NPD (50 nm)/BCP (20 nm)/Alq 3 (50 nm)

When the thus-prepared color organic EL display apparatus was driven, desired color image data can be displayed stably with good image qualities.

EXAMPLE 12

Synthesis of Ex. Comp. No. 31

It is easy to synthesize the following compound in the same manner as in Example 1 except for using 2-bromopyridine (made by Tokyo Kasei Kogyo K.K.) instead of 2-chloro-5-trifluoromethylpyridine in Example 1.

Tris[2-(benzofuran-2-yl)pyridine-C³,N]iridium (III).

EXAMPLE 13

Synthesis of Ex. Comp. No. 32

It is easy to synthesize the following compound in the same manner as in Example 1 except for using 2-chloro-4-trifluoromethylpyridine (made by Florochem USA) instead of 2-chloro-5-trifluoromethylpyridine in Example 1.

Tris[2-(benzofuran-2-yl)-4-trifluoromethyl-pyridine-C³, N]iridium (III).

EXAMPLE 14

Synthesis of Ex. Comp. No. 33

It is easy to synthesize the following compound in the same manner as in Example 1 except for using 2-chloro-4, 5-bis(trifluoro-methyl)pyridine (made by Oakwood Products Inc.) instead of 2-chloro-5-trifluoromethylpyridine in Example 1.

Tris[2-(benzofuran-2-yl)-4,5-bis(trifluoro-methyl) pyridine-C³, N]iridium (III).

EXAMPLE 15

Synthesis of Ex. Comp. No. 35

It is easy to synthesize the following compound in the same manner as in Example 16 except for using 4-phenyl-2-bromopyridine (made by General Intermediates of Canada) instead of 2-chloro-5-trifluoromethylpyridine in Example 1.

Tris[2-(benzofuran-2-yl)-4-pyridine-C³,N]-iridium (III).

EXAMPLE 16

Synthesis of Ex. Comp. No. 36

It is easy to synthesis the following compound in the same manner as in Example 1 except that 2-(benzofuran-2-yl)-5-bromopyridine was synthesized from 2,5-dibromopyridine (made by Tokyo Kasei Kogyo K.K.) and 2-benzofuranboronic acid (made by Aldrich Co.) and is reacted with 1-naphthylboronic acid (made by Tokyo Kasei Kogyo) to obtain 2-(benzofuran-2-yl)-5-(naphthalene-1-yl)pyridine, which is used instead of 2-(5-trifluoromethylpyridine-2-yl)benzofuran.

Tris[2-(benzofuran-2-yl)-5-(naphthalene-1-yl)pyridine-$C^3$,N]iridium (III).

EXAMPLE 17

Synthesis of Ex. Comp. No. 42

It is easy to synthesize the following compound in the same manner as in Example 16 except for using 2-naphthylboronic acid (made by Tokyo Kasei Kogyo K.K.) instead of 1-naphthylboronic acid in Example 16.

Tris[2-(benzofuran-2-yl)-5-(naphthalene-2-yl)pyridine-$C^3$, N]iridium (III).

EXAMPLE 18

Synthesis of Ex. Comp. No. 47

It is easy to synthesize the following compound in the same manner as in Example 1 except for reacting 2 equivalent amount of 2-benzofuran boronic acid (made by Aldrich Co.) with 2,5-dibromopyridine (made by Tokyo Kasei Kogyo K.K.) to synthesis 2,5-bis(benzofuran-2-yl)pyridine, which is used instead of 2-(5-trifluoromethylpyridine-2-yl)benzofuran, in Example 1.

Tris[2,5-bis(benzofuran-2-yl)pyridine-$C^3$,N]iridium (III).

EXAMPLE 19

Synthesis of Ex. Comp. No. 50

It is easy to synthesis the following compound in the same manner as in Example 1 except that 2-(benzofuran-2-yl)-5-bromopyridine was synthesized from 2,5-dibromopyridine (made by Tokyo Kasei Kogyo K.K.) and 2-benzofuranboronic acid (made by Aldrich Co.) and is reacted with 3-thiopheneboronic acid (made by Aldrich Co.) to obtain 2-(benzofuran-2-yl)-5-(thiophene-3-yl)pyridine, which is used instead of 2-(5-trifluoromethylpyridine-2-yl)benzofuran.

Tris[2-(benzofuran-2-yl)-5-(thiophene-3-yl)pyridine-$C^3$, N]iridium (III).

EXAMPLE 20

An organic EL device shown in FIG. 1C was prepared in the following manner.

On a 100 nm-thick patterned ITO electrode (anode) formed on a 1.1 mm-thick no-alkali glass substrate, a 40 nm-thick charge transport layer of α-NPD was formed by vacuum deposition ($10^{-4}$ Pa) at a deposition rate of 0.1 nm/sec. On the charge transport layer, a 40 nm-thick luminescence layer (co-deposited film) of CBP: iridium complex of Ex. Comp. No. 34 prepared in Example 1 (97:3 by weight) was formed by co-vacuum deposition at deposition rates of 0.1 nm/sec (for CBP) and 0.08 nm/sec (for the iridium complex) by controlling heating conditions of deposition vessel. On the luminescence layer, a 10 nm-thick exciton diffusion prevention layer of BCP (Bathocuproine) was formed by vacuum deposition at a deposition rate of 0.1 nm/sec, and or the exciton diffusion prevention layer, a 20 nm-thick electron transport layer of Alq 3 was formed by vacuum deposition at a deposition rate of 0.1 nm/sec. Thereafter, or the electron transport layer, a 150 nm-thick aluminum electrode (cathode) was formed by vacuum deposition at a deposition rate of 1 nm/sec.

The thus-prepared organic EL device exhibited an EL spectrum showing λmax=625 nm and luminescent efficiencies of 1.5 lm/W at a luminance of 100 cd/m².

EXAMPLE 21

Synthesis of Ex. Comp. No. 62

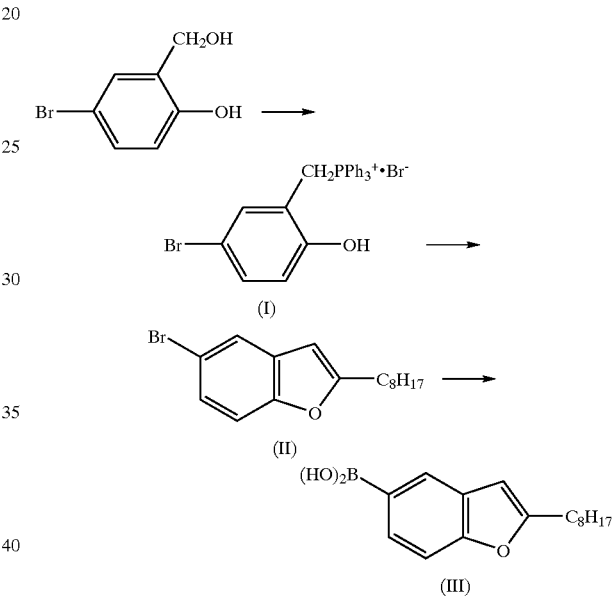

In a 2 liter-three-necked flask, 145.8 g (718 mM) of 5-bromo-2-hydroxybenzyl alcohol, 246.5 g (718 mM) of triphenyl phosphine.HBr, and 730 ml of acetonitrile were placed and refluxed under stirring for 3 hours. The reaction liquid was cooled down to room temperature to precipitate a crystal of 5-bromo-2-hydroxybenzyltriphenylphosphonium bromide (I), which was recovered by filtration (Yield: 362.0 g (95.5%)).

In a 1 liter-three-necked flask, 50.0 g (94.7 mM) o the phosphonium bromide (I), 31.1 g (104 mM) of 1-nonanoic acid anhydride, 450 ml of toluene and 39.6 g (392 mM) of triethylamine were placed and refluxed under stirring for 6 hours. The reaction liquid was cooled down to room temperature to precipitate a crystal, which was filtered out. The solvent of the filtrate was distilled off under reduced pressure to obtain a residue. The residue was purified by silica gel column chromatography (eluent: hexane) to a colorless oily product of 2-octyl-5-bromobenzofuran (II) (Yield: 25.1 g (85.8%)).

In a 500 ml-three-necked flask, 19.0 g (61.5 mM) of 2-octyl-5-bromobenzofuran (II) and 190 ml of anhydrous tetrahydrofuran (THF) were placed. To the mixture, 45 ml (72.0 mM) of 1.6M-n-butyllithium solution in hexane was added dropwise under argon stream at −70° C. or below in 30 min., followed by stirring at that temperature for 4 hours. To the resultant mixture, a solution of 17.8 g (171 mM) of trimethylborate in 70 ml of anhydrous THF was added dropwise at −70° C. or below in 20 min., and stirred at that temperature for 2 hours. The system was heated up to room temperature and stirred for 17 hours. To the reaction mixture, 100 ml of 10%-hydrochloric acid was added dropwise, followed by extraction with ether. The organic layer was washed with water and dried with anhydrous sodium sulfate, followed by distilling-off of the solvent under reduced pressure to obtain a residue. The residue was purified by silica gel column chromatography (eluent: hexane/ethyl acetate=4/1) to obtain a white crystal of 2-octylbenzofuran-5-boronic acid (III) (Yield: 10.8 g (64.1%)).

It is easy to synthesize the following compound in the same manner as in Example 1 except for using 2-octylbenzofuran-5-boronic acid (III) instead of 2-benzofuran boronic acid in Example 1.

Tris[2-(2-octylbenzofuran-5-yl)pyridine-C³,N]iridium (III).

EXAMPLE 22

Synthesis of Ex. Comp. No. 61

It is easy to synthesis the following compound in the same manner as in Example 1 except for using, instead of 2-(5-trifluoromethylpyridine-2-yl)benzofuran, 2-phenyl-5-(5-tifluoromethylpyridine-2-yl)benzofuran synthesized in the same manner as in Example 21 except that 2-phenyl-5-bromobenzofuran was synthesized from benzoic acid chloride used instead of 1-nonanoic acid and 2-phenyl-5-(5-trifluoromethyl-pyridine-2-yl)benzofuran was synthesized from 2-phenyl-5-bromobenzofuran.

Tris[2-(2-phenylbenzofuran-5-yl)-5-trifluoro-methylpyridine-C³, N]iridium (III).

EXAMPLE 23

Synthesis of Ex. Comp. No. 72

4-bromo-2-hydroxybenzyl alcohol (IV) is synthesized from 4-aminosalicylic acid (made by Aldrich Co.) in the following reaction scheme, and 4-bromo-2-hydroxybenzyltriphenylphosphon bromide (V) is synthesized in the same manner as in Example 21.

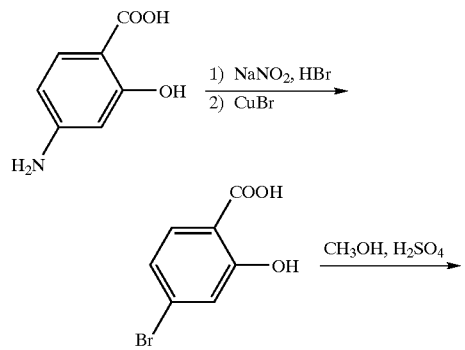

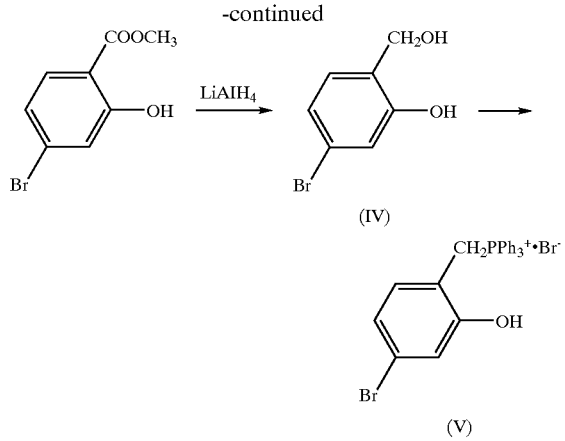

It is easy to synthesize the following compound in the same manner as in Example 21 except for using 1-butanoic acid anhydrate instead of 1-nonanoic acid anhydrate in Example 21.

Tris[2-(2-propylbenzofuran-6-yl)pyridine-C⁵,N]iridium (III).

As described above, according to the present invention, the metal coordination compound of the formula (1) characterized by the benzofuran structure of the formula (5) as a partial structure is an excellent material which exhibits a high emission quantum efficiency. The electroluminescence device (luminescence device) of the present invention using, as a luminescent center material, the metal coordination compound of the formula (1) is an excellent device which not only allows high-efficiency luminescence but also retains a high luminance for a long period and shows little deterioration by current passage. Further, the display apparatus using the electroluminescence device of the present invention exhibits excellent display performances.

What is claimed is:
1. A metal coordination compound represented by formula (1) below:

wherein M is a metal atom of Ir, Pt, Rh or Pd; L and L' are mutually different bidentate ligands; m is 1, 2 or 3 and n is 0, 1 or 2 with the proviso that m+n is 2 or 3; a partial structure $ML_m$ is represented by formula (2) shown below and a partial structure $ML'_n$ is represented by formula (3) or (4) shown below:

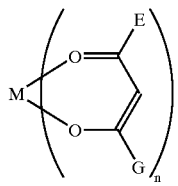

(4)

wherein CyN1 and CyN2 are each cyclic group capable of having a substituent, including a nitrogen atom and bonded to the metal atom M via the nitrogen atom; CyC1 and CyC2 are each cyclic group capable of having a substituent, including a carbon atom and bonded to the metal atom M via the carbon atom with the proviso that the cyclic group CyN1 and the cyclic group CyC1 are bonded to each other via a covalent bond and the cyclic group CyN2 and the cyclic group CyC2 are bonded to each other via covalent bond;

the optional substituent of the cyclic groups is selected from a halogen atom, cyano group, a nitro group, a trifluoromethyl group, a trialkylsilyl group of which the alkyl groups are independently a linear or branched alkyl group having 1 to 8 carbon atoms, a linear or branched alkyl group having 2 to 20 carbon atoms of which the alkyl group can include one or non-neighboring two or more methylene groups that can be replaced with —O—,—S—, —CO—, —CO—O—, —O—CO—, —CH=CH— or —C≡C—, and the alkyl group can include a hydrogen atom that can be optionally replaced with a fluorine atom, or an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom);

E and G are independently a linear or branched alkyl group having 1 to 20 carbon atoms of which the alkyl group can include a hydrogen atom that can be optionally replaced with a fluorine atom, or an aromatic group capable of having a substituent (that is a halogen atom, a cyano atom, a nitro atom, a trialkylsilyl group of which the alkyl groups are independently a linear or branched alkyl group having 1–8 carbon atoms, a linear or branched alkyl group having 1 to 20 carbon atoms of which the alkyl group can include one or non-neighboring two or more methylene groups that can be replaced with —O—, —S—, —CO—, —CO—O—, —O—CO—, —CH=CH— or —C≡C—, and the alkyl group can include a hydrogen atom that can be optionally replaced with a fluorine atom; and at least one of the cyclic groups CyC1 and CyC2 includes a benzofuran structure capable of having a substituent represented by the following formula (5):

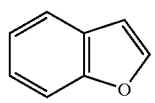

(5)

wherein the benzofuran structure of the formula (5) is bonded to CyN1 or CyN2 via a single bond at any one of 2- to 7-positions and bonded to the metal atom M via a single bond at any one of 2- to 7-positions;

the optional substituent of the benzofuran structure of the formula (5) is selected from a halogen atom, cyano group, a nitro group, a trifluoromethyl group, a trialkylsilyl group of which the alkyl groups are independently a linear or branched alkyl group having 1 to 8 carbon atoms, a linear or branched alkyl group having 2 to 20 carbon atoms of which the alkyl group can include one or non-neighboring two or more methylene groups that can be replaced with —O—,—S—, —CO—, —CO—O—, —O—CO—, —CH=CH— or —C≡C—, and the alkyl group can include a hydrogen atom that can be optionally replaced with a fluorine atom, or an aromatic group capable of having a substituent (that is a halogen atom, a cyano atom, a nitro atom, a linear or branched alkyl group having 1 to 20 carbon atoms of which the alkyl group can include one or non-neighboring two or more methylene groups that can be replaced with —O—,—S—, —CO—, —CO—O—, —O—CO—, —CH=CH— or —C≡C—, and the alkyl group can include a hydrogen atom that can be optionally replaced with a fluorine atom) with the proviso that an adjacent pair of substituents located at 4- to 7-positions of the benzofuran structure of the formula (5) can be bonded to form a cyclic structure.

2. A metal coordination compound according to claim 1, wherein n is 0 in the formula (1).

3. A metal coordination compound according to claim 1, including a partial structure $ML'_n$ represented by the formula (3) in the formula (1).

4. A metal coordination compound according to claim 1, including a partial structure $ML'_n$ represented by the formula (4) in the formula (1).

5. A metal coordination compound according to claim 1, wherein the cyclic groups CyC1 and CyC2 are independently selected from phenyl group, thienyl group, thianaphthyl group, naphthyl group, pyrenyl group, 9-fluorenonyl group, fluorenyl group, dibenzofuranyl group, dibenzothienyl group, carbazolyl group, or benzofuranyl group, as an aromatic cyclic group capable of having a substituent with the proviso that the aromatic cyclic group can include one or two CH groups that can be replaced with a nitrogen atom.

6. A metal coordination compound according to claim 5, wherein the cyclic groups CyC1 and Cy2 are independently phenyl group or benzofuranyl group.

7. A metal coordination compound according to claim 1, wherein the cyclic groups CyN1 and CyN2 are independently selected from pyridyl group, pyridazinyl group, and pyrimidinyl group, as an aromatic cyclic group capable of having a substituent.

8. A metal coordination compound according to claim 7, wherein the aromatic cyclic group is pyridyl group.

9. A metal coordination compound according to claim 1, wherein the cyclic groups CyN1, CyN2, CyC1 and CyC2 are independently non-substituted, or have a substituent selected from a halogen atom, a trifluoromethyl group, and a linear or branched alkyl group having 2 to 20 carbon atoms of which the alkyl group can include one or non-neighboring two or more methylene groups that can be replaced with —O—, —S—, —CO—, —CH=CH—, —C≡C—, or a divalent aromatic group capable of having a substituent (that is a halogen atom or a linear or branched alkyl group having 1 to 20 carbon atoms (of which the alkyl group can include one or non-neighboring two or more methylene groups that can be replaced with —O—, and the alkyl group can include a hydrogen atom that can be optionally replaced with a fluorine atom)), and the alkyl group can include a hydrogen atom that can be optionally replaced with a fluorine atom.

10. A metal coordination compound according to claim 1, wherein M in the formula (1) is iridium.

11. A metal coordination compound according to claim 1, which is represented by the following formula (6) or (7):

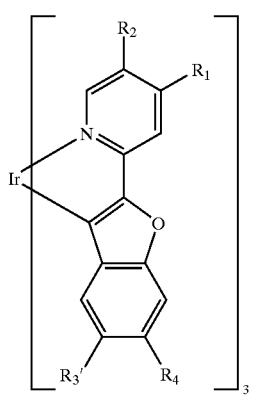

(6)

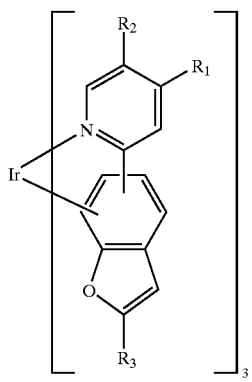

(7)

wherein $R_1$, $R_2$, $R_3$, $R'_3$ and $R_4$ are independently a hydrogen atom; a fluorine atom; a trifluoromethyl group; a linear or branched alkyl group of formula: $C_nH_{2n+1}$— in which n is an integer of 2–20, the alkyl group can include one or non-neighboring two or more methylene groups that can be replaced with —O— and also can include a hydrogen atom that can be optionally replaced with a fluorine atom; a phenyl group capable of having a substituent; or a benzofuranyl group capable of having a substituent; the optional substituent of phenyl group and benzofuranyl group is a fluorine atom or a linear or branched alkyl group of formula: $C_nH_{2n+1}$— in which n is an integer of 1–20, the alkyl group can include one or non-neighboring two or more methylene groups that can be replaced with —O— and also can include a hydrogen atom that can be optionally replaced with a fluorine atom.

12. An electroluminescence device, comprising: a pair of electrodes disposed on a substrate, and a luminescence unit comprising at least one organic compound disposed between the electrodes, wherein the organic compound comprises a metal coordination compound represented by the formula (1) in claim 1.

13. An electroluminescence device according to claim 12 wherein a voltage is applied between the electrodes to emit phosphorescence.

14. A picture display apparatus, comprising an electroluminescence device according to claim 12, and a means for supplying electric signals to the electroluminescence device.

* * * * *